(12) United States Patent
Feucht et al.

(10) Patent No.: US 8,648,014 B2
(45) Date of Patent: Feb. 11, 2014

(54) HERBICIDES CONTAINING SUBSTITUTED THIEN-3-YL-SULPHONYLAMINIO(THIO)CARBONYL-TRIAZOLIN(ETHI)ONES

(75) Inventors: Dieter Feucht, Eschborn (DE); Peter Dahmen, Neuss (DE); Mark Wilhelm Drewes, Langenfeld (DE); Rolf Pontzen, Leichlingen (DE); Rudolf Ernst Gesing, Erkrath-Hochdahl (DE)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 13/588,000

(22) Filed: Aug. 17, 2012

(65) Prior Publication Data
US 2012/0309622 A1 Dec. 6, 2012

Related U.S. Application Data

(62) Division of application No. 12/824,951, filed on Jun. 28, 2010, now Pat. No. 8,268,752, which is a division of application No. 10/489,086, filed as application No. PCT/EP02/26426 on Sep. 10, 2002, now Pat. No. 7,781,374.

(30) Foreign Application Priority Data

Sep. 21, 2001 (DE) .................................. 101 46 591

(51) Int. Cl.
*A01N 43/647* (2006.01)
*A01N 47/38* (2006.01)

(52) U.S. Cl.
USPC .......................................... 504/139; 504/273

(58) Field of Classification Search
USPC .................................. 504/139, 273
See application file for complete search history.

(56) References Cited

U.S. PATENT DOCUMENTS

| | | |
|---|---|---|
| 4,639,266 A | 1/1987 | Heubach et al. |
| 4,881,966 A | 11/1989 | Nyffeler et al. |
| 5,494,886 A | 2/1996 | Kehne et al. |
| 5,529,976 A | 6/1996 | Kehne et al. |
| 5,576,440 A | 11/1996 | Kehne et al. |
| 5,635,451 A | 6/1997 | Kehne et al. |
| 5,698,493 A | 12/1997 | Lake et al. |
| 5,700,758 A | 12/1997 | Rosch et al. |
| 5,703,008 A | 12/1997 | Rosch et al. |
| 5,750,718 A | 5/1998 | Mueller et al. |
| 5,846,907 A | 12/1998 | Von Deyn et al. |
| 6,077,813 A | 6/2000 | Linker et al. |
| 6,121,204 A | 9/2000 | Mueller et al. |
| 6,124,469 A | 9/2000 | Rheinheimer et al. |
| 6,331,507 B1 | 12/2001 | Linker et al. |
| 6,420,316 B1 | 7/2002 | Linker et al. |
| 6,451,736 B1 | 9/2002 | Linker et al. |
| 6,964,939 B1 * | 11/2005 | Gesing et al. .................. 504/273 |
| 2002/0025910 A1 | 2/2002 | Von Deyn et al. |

FOREIGN PATENT DOCUMENTS

| | | |
|---|---|---|
| CA | 2 388 745 | 4/2001 |
| EP | 0 303 153 | 2/1989 |
| GB | 820180 | 9/1959 |
| JP | 63-72605 | 4/1988 |
| WO | 01/05788 | 1/2001 |

OTHER PUBLICATIONS

S.R. Colby; "Calculating Synergistic and Antagonistic Responses of Herbicide Combinations"; Weeds; 1967; vol. 15; pp. 20-22.

* cited by examiner

*Primary Examiner* — Kortney L Klinkel
(74) *Attorney, Agent, or Firm* — Miles & Stockbridge P.C.

(57) ABSTRACT

The invention relates to herbicidal compositions, their preparation, and their use for controlling unwanted vegetation. The compositions include an effective amount of an active compound combination that includes:
(a) a substituted thien-3-yl-sulphonylaminocarbonyltriazolinone of formula (I-2)

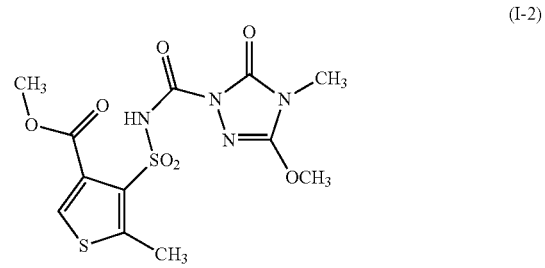

or salts thereof; and
(b) at least one of the known herbicides listed in the disclosure and,
(c) optionally a safener.

4 Claims, No Drawings

HERBICIDES CONTAINING SUBSTITUTED THIEN-3-YL-SULPHONYLAMINIO(THIO)CARBONYL-TRIAZOLIN(ETHI)ONES

This application is a divisional application of U.S. application Ser. No. 12/824,951, filed Jun. 28, 2010, which is a divisional application of U.S. patent application Ser. No. 10/489,086, filed on Aug. 12, 2004, which was filed under 35 U.S.C. 371 as a national stage application of PCT/EP02/10103, filed Sep. 10, 2002, which was published in German as International Patent Publication WO 03/026426 on Apr. 3, 2003, which is entitled to the right of priority of German Patent Application 101 46 591.2, filed Sep. 21, 2001. All of these are hereby incorporated by reference in their entireties.

The invention relates to novel herbicidal synergistic active compound combinations comprising known substituted thien-3-yl-sulphonylamino(thio)carbonyltriazolin(ethi)-ones and one or more known herbicidally active compounds and, if appropriate, additionally a crop-plant-compatibility-improving compound, which combinations can be used with particularly good results for controlling weeds in various crops of useful plants or else for controlling monocotyledonous and dicotyledonous weeds in the semi- and nonselective field.

Substituted thien-3-yl-sulphonylamino(thio)carbonyltriazolin(ethi)ones are known to be effective herbicides (cf. WO-A-01/05788). However, the activity of these compounds is not always entirely satisfactory.

Surprisingly, it has now been found that a number of active compounds from the group of the substituted thien-3-yl-sulphonylamino(thio)carbonyltriazolin(ethi)ones, when used together with certain herbicidally active compounds, show synergistic effects with respect to the activity against weeds and can be used particularly advantageously as broadly active combination preparations for the selective control of mono-cotyledonous and dicotyledonous weeds in crops of useful plants, such as, for example, in cotton, barley, potatoes, maize, oil seed rape, rice, rye, soy beans, sunflowers, wheat, sugar cane and sugar beet, but also for controlling monocotyledonous and dicotyledonous weeds in the semi- and nonselective field.

The invention provides herbicidal compositions, characterized by an effective amount of an active compound combination comprising a) at least one substituted thien-3-yl-sulphonylamino(thio)carbonyltriazolin-(ethi)one of the general formula (I)

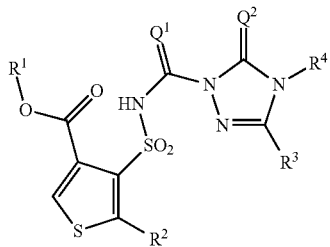

(I)

in which $Q^1$ represents O (oxygen) or S (sulphur),
$Q^2$ represents O (oxygen) or S (sulphur),
$R^1$ represents optionally cyano-, halogen- or $C_1$-$C_4$-alkoxy-substituted alkyl having 1 to 6 carbon atoms, or represents in each case optionally cyano- or halogen-substituted alkenyl or alkynyl having in each case 2 to 6 carbon atoms, or represents in each case optionally cyano-, halogen- or $C_1$-$C_4$-alkyl-substituted cycloalkyl or cycloalkylalkyl having in each case from 3 to 6 carbon atoms in the cycloalkyl group and, if appropriate, 1 to 4 carbon atoms in the alkyl moiety, represents in each case optionally nitro-, cyano-, halogen-, $C_1$-$C_4$-alkyl- or $C_1$-$C_4$-alkoxy-substituted aryl or arylalkyl having in each case 6 or 10 carbon atoms in the aryl group and, if appropriate, 1 to 4 carbon atoms in the alkyl moiety, or represents in each case optionally nitro-, cyano-, halogen-, $C_1$-$C_4$-alkyl- or $C_1$-$C_4$-alkoxy-substituted heterocyclyl or heterocyclylalkyl having in each case up to 6 carbon atoms and additionally 1 to 4 nitrogen atoms and/or 1 or 2 oxygen or sulphur atoms in the heterocyclyl group and, if appropriate, 1 to 4 carbon atoms in the alkyl moiety, $R^2$ represents hydrogen, cyano, nitro, halogen, or represents in each case optionally cyano-, halogen- or $C_1$-$C_4$-alkoxy-substituted alkyl, alkoxy, alkoxycarbonyl, alkylthio, alkylsulphinyl or alkylsulphonyl having in each case 1 to 6 carbon atoms in the alkyl group, or represents in each case optionally cyano- or halogen-substituted alkenyl, alkynyl, alkenyloxy or alkynyloxy having in each case 2 to 6 carbon atoms in the alkenyl or alkynyl group, $R^3$ represents hydrogen, hydroxyl, mercapto, amino, cyano, fluorine, chlorine, bromine, iodine, represents optionally fluorine-, chlorine-, bromine-, cyano-, $C_1$-$C_4$-alkoxy-, $C_1$-$C_4$-alkyl-carbonyl- or $C_1$-$C_4$-alkoxy-carbonyl-substituted alkyl having 1 to 6 carbon atoms, represents in each case optionally fluorine-, chlorine- and/or bromine-substituted alkenyl or alkynyl having in each case 2 to 6 carbon atoms, represents in each case optionally fluorine-, chlorine-, cyano-, $C_1$-$C_4$-alkoxy- or $C_1$-$C_4$-alkoxy-carbonyl-substituted alkoxy, alkylthio, alkyl-amino or alkylcarbonylamino having in each case 1 to 6 carbon atoms in the alkyl group, represents alkenyloxy, alkynyloxy, alkenylthio, alkynylthio, alkenylamino or alkynylamino having in each case 3 to 6 carbon atoms in the alkenyl or alkynyl group, or represents dialkyl-amino having in each case 1 to 4 carbon atoms in the alkyl groups, or represents in each case optionally methyl- and/or ethyl-substituted aziridino, pyrrolidino, piperidino or morpholino, or represents in each case optionally fluorine-, chlorine-, bromine-, cyano- and/or $C_1$-$C_4$-alkyl-substituted cycloalkyl, cycloalkenyl, cycloalkyloxy, cycloalkyl-thio, cycloalkylamino, cycloalkylalkyl, cycloalkylalkoxy, cycloalkyl-alkylthio or cycloalkylalkylamino having in each case 3 to 6 carbon atoms in the cycloalkyl or cycloalkenyl group and, if appropriate, 1 to 4 carbon atoms in the alkyl moiety, or represents in each case optionally fluorine-, chlorine-, bromine-, cyano-, nitro-, $C_1$-$C_4$-alkyl-, trifluoromethyl-, $C_1$-$C_4$-alkoxy- and/or $C_1$-$C_4$-alkoxy-carbonyl-substituted aryl, arylalkyl, aryloxy, arylalkoxy, arylthio, arylalkylthio, arylamino or arylalkylamino having in each case 6 or 10 carbon atoms in the aryl group and, if appropriate, 1 to 4 carbon atoms in the alkyl moiety, $R^4$ represents hydrogen, hydroxyl, amino, cyano, or represents $C_2$-$C_{10}$-alkylideneamino, or represents optionally fluorine-, chlorine-, bromine-, cyano-, $C_1$-$C_4$-alkoxy-, $C_1$-$C_4$-alkyl-carbonyl- or $C_1$-$C_4$-alkoxy-carbonyl-substituted alkyl having 1 to 6 carbon atoms, or represents in each case optionally fluorine-, chlorine- and/or bromine-substituted alkenyl or alkynyl having in each case 2 to 6 carbon atoms, or represents in each case optionally fluorine-, chlorine-, bromine-, cyano-, $C_1$-$C_4$-alkoxy- or $C_1$-$C_4$-alkoxy-carbonyl-substituted alkoxy, alkylamino or alkyl-carbonylamino having in each case 1 to 6 carbon atoms in the alkyl group, or represents alkenyloxy having 3 to 6 carbon atoms, or represents dialkylamino having in each case 1 to 4 carbon atoms in the alkyl groups, or represents in each case optionally fluorine-, chlorine-, bromine-, cyano- and/or $C_1$-$C_4$-alkyl-substituted cycloalkyl, cycloalkylamino or cycloalkylalkyl having in each case 3 to 6 carbon atoms in the alkyl group and, if appropriate, 1 to 4 carbon atoms in the alkyl moiety, or represents in each case optionally fluorine-, chlorine-, bromine-, cyano-, nitro-, $C_1$-$C_4$-alkyl-, trifluoro-methyl- and/or $C_1$-$C_4$-alkoxy-substituted aryl or arylalkyl having in each case 6 or 10 carbon atoms in the aryl group and, if appropriate, 1 to 4 carbon atoms in the alkyl moiety, or $R^3$ and $R^4$ together represent optionally branched alkanediyl having 3 to 6 carbon atoms,
—and salts of the compounds of the formula (I)—
("Active compounds of Group 1")
and b) one or more compounds of a second group of herbicides consisting of the active compounds below:
4,5-dihydro-3-methoxy-4-methyl-5-oxo-N-[(2-trifluoromethoxyphenyl)-sulphonyl]-1-H-1,2,4-triazole-1-carboxamide sodium salt (flucarbazone-sodium), 2-chloro-N-(ethoxymethyl)-N-(2-ethyl-6-methylphenyl)acetamide (acetochlor), 5-(2-chloro-4-trifluoromethylphenoxy)-2-nitrobenzoic acid (sodium salt) (acifluorfen (-sodium)), 2-chloro-6-nitro-3-phenoxybenzenamine (aclonifen), 2-chloro-N-(methoxymethyl)-N-(2,6-diethylphenyl)acetamide (alachlor), methyl 4-hydroxy-6,6-dimethyl-2-oxo-3-[1-[(2-propenyl-oxy)imino]butyl]-3-cyclohexene-1-carboxylate (sodium salt) (alloxydim (-sodium)), N-ethyl-N'-isopropyl-6-methylthio-1,3,5-triazine-2,4-diamine (ametryn), 4-amino-N-(1,1-dimethylethyl)-4,5-dihydro-3-(1-methylethyl)-5-oxo-1H-1,2,4-triazole-1-carboxamide (amicarbazone), N-(4,6-di-methoxypyrimidin-2-yl)-N'—(N-methyl-N-methylsulphonylsulphamoyl)urea (amidosulfuron), 1H-1,2,4-triazole-3-amine (amitrole), S-[2-[(4-chlorophenyl)-(1-isopropyl)amino]-2-oxoethyl] O,O-dimethyl phosphoro-dithioate (anilofos), O-methyl N-(4-aminophenylsulphonyl)carbamate (asulam), 6-chloro-4-ethylamino-2-isopropylamino-1,3,5-triazine (atrazine), 2-[2,4-dichloro-5-(2-propynyloxy)phenyl]-5,6,7,8-tetrahydro-1,2,4-triazolo-[4,3-a]-pyridin-3 (2H)-one (azafenidin), N-(4,6-dimethoxypyrimidin-2-yl)-N'-[1-methyl-4-(2-methyl-2H-tetrazol-5-yl)-1H-pyrazol-5-ylsulphonyl]urea (azimsulfuron), N-benzyl-2-(4-fluoro-3-trifluoromethylphenoxy)butanamide (beflubutamid), 4-chloro-2-oxo-3(2H)-benzothiazoleacetic acid (ethyl ester) (benazolin, (-ethyl)), N-butyl-N-ethyl-2,6-dinitro-4-trifluoromethylbenzenamine (benfluralin), 2,3-dihydro-3,3-dimethyl-5-benzofuranylethanesulphonate (benfuresate), N-(4,6-dimethoxypyrimidin-2-yl)-N'-(2-methoxy-carbonylphenylmethylsulphonyl)urea (bensulfuron-methyl), 3-i-propyl-1H-2,1,3-benzothiadiazin-4(3H)-one 2,2-dioxide (bentazone), S-[(4-chlorophenyl)methyl]diethylthiocarbamate (benthiocarb, Thiobencarb), methyl 2-[2-[4-(3,6-dihydro-3-methyl-2,6-dioxo-4-trifluoromethyl-1(2H)-pyrimidinylphenoxymethyl]-5-ethylphenoxypropanoate (benzfendizone), 3-(2-chloro-4-methylsulphonylbenzoyl)-4-phenylthiobicyclo-[3.2.1]-oct-3-ene-2-one (benzobicyclon), 2-[[4-(2,4-dichloro-3-methylbenzoyl)-1,3-dimethyl-1H-pyrazol-5-yl]oxy]-1-(4-methylphenyl)ethanone (benzofenap), methyl 5-(2,4-dichlorophenoxy)-2-nitrobenzoate (bifenox), 2,6-bis-(4,6-dimethoxypyrimidin-2-yl-oxy) benzoic acid sodium salt (bispyribac-sodium), 5-bromo-6-methyl-3-(1-methylpropyl)-2,4(1H,3H)-pyrimidinedione (bromacil), 2-bromo-3,3-dimethyl-N-(1-methyl-1-phenylethyl)butanamide (bromobutide), 3,5-dibromo-4-hydroxybenzaldehyde O-(2,4-dinitrophenyl)oxime (bromofenoxim), 3,5-dibromo-4-hydroxybenzonitrile (bromoxynil), N-butoxymethyl-2-chloro-N-(2,6-diethylphenyl)acetamide (butachlor), 1,1-dimethyl-2-oxo-2-(2-propenyloxy)]ethyl 2-chloro-5-(3,6-dihydro-3-methyl-2,6-dioxo-4-trifluoromethyl-1(2H)-pyrimidinyl)benzoate (butafenacil), 4-(1-t-butyl)-N-(s-butyl)-2,6-dinitroaniline (butralin), 2-(1-ethoximinopropyl)-3-hydroxy-5-[2,4,6-trimethyl-3-(1-oxobutyl)phenyl]-2-cyclohexene-1-one (butroxydim), S-ethyl bis-(2-methylpropyl)thiocarbamate (butylate), N,N-diethyl-3-(2,4,6-trimethylphenylsulphonyl)-1H-1,2,4-triazole-1-carboxamide (cafenstrole), (R)—N-ethyl-2-[(phenylaminocarbonyl)oxy]propanamide (carbetamide), 2-(4-chloro-2-fluoro-5-(2-chloro-2-ethoxycarbonylethyl)phenyl)-4-difluoromethyl-5-methyl-2,4-dihydro-3H-1,2,4-triazol-3-one (carfentrazone-ethyl), 2,4-dichloro-1-(3-methoxy-4-nitrophenoxy)benzene (chlormethoxyfen), 5-amino-4-chloro-2-phenyl-3(2H)-pyridazinone (chloridazon), N-(4-chloro-6-methoxypyrimidin-2-yl)-N'-(2-ethoxycarbonylphenylsulphonyl)urea (chlorimuron-ethyl), 1,3,5-trichloro-2-(4-nitrophenoxy)benzene (chlornitrofen), N'-(3-chloro-4-methylphenyl)-N,N-dimethylurea (chlorotoluron), N-(4-methoxy-6-methyl-1,3,5-triazin-2-yl)-N'-(2-chlorophenyl-sulphonyl)urea (chlorsulfuron), ethyl 2-chloro-3-[2-chloro-5-(1,3,4,5,6,7-hexahydro-1,3-dioxo-2H-isoindol-2-yl)phenyl]-2-propanoate (cinidon-ethyl), exo-1-methyl-4-isopropyl-2-(2-methylphenylmethoxy)-7-oxabicyclo-[2.2.1]-heptane (cinmethylin), N-(4,6-dimethoxy-1,3,5-triazin-2-yl)-N'-(2-(2-meth-oxyethoxy)phenylsulphonyl)urea (cinosulfuron), 2-[1-[2-(4-chlorophen-oxy)propoxyaminobutyl]-5-(tetrahydro-2H-thiopyran-3-yl)-1,3-cyclohexanedione (clefoxydim), (E,E)-(+)-2-[1-[[(3-chloro-2-pro-penyl)oxy]imino]propyl]-3-hydroxy-2-cyclohexen-1-one (clethodim), (R)-(2-propyinyl) 2-[4-(5-chloro-3-fluoropyridin-2-yl-oxy) phenoxypropanoate (clo-dinafop-propargyl), 2-[(2-chlorophenyl)methyl]-4,4-dimethyl-3-isoxazol-idinone (clomazone), 2-(2,4-dichloro3-methylphenoxy)-N-phenylpropanamide (clomeprop), 3,6-dichloropyridin-2-carboxylic acid (clopyralid), methyl 3-chloro-2-[(5-ethoxy-7-fluoro[1,2,4]triazolo[1,5-c]pyrimidin-2-ylsulph-onyl)amino]benzoate (cloransulam-methyl), N-[(2-chlorophenyl)methyl]-N'-(1-methyl-1-phenylethyl)urea (cumyluron), 2-chloro-4-ethylamino-6-(1-cyano-1-methylethylamino)-1,3,5-triazine (cyanazine), N-(4,6-di-methoxypyrimidin-2-yl)-N'-(2-cyclopropyl-carbonylphenylsulphonyl)urea (cyclosulfamuron), 2-(1-ethoximinobutyl)-3-hydroxy-5-(tetrahydro-2H-thiopyran-3-yl)-2-cyclohexen-1-one (cycloxydim), (R)-butyl 2-[4-(4-cyano-2-fluorophenoxy)phenoxy]propanoate (cyhalofop-butyl), 2,4-dichlorophenoxyacetic acid (2,4-D), O-ethyl N-[3-(phenylaminocarbonyl-oxy) phenyl]carbamate (desmedipham), 3,6-dichloro-2-methoxybenzoic acid (dicamba), 2,6-dichlorobenzonitrile (dichlobenil), (R)-2-(2,4-dichlorophen-oxy) propanoic acid (dichlorprop-P), methyl 2-[4-(2,4- dichlorophenoxy)phenoxy]propanoate (diclofop-methyl), N-(2,6-dichlorophenyl)-5-ethoxy-7-fluoro-[1,2,4]-triazolo-[1,5-c]-pyrimidine-2-sulphonamide (diclosulam), 1,2-dimethyl-3,5-diphenyl-1H-pyrazolium methylsulphate (difenzoquat), N-(2,4-difluorophenyl)-2-(3-trifluoromethylphenoxy)pyridine-3-carboxamide (diflufenican), 2-[1-[(3,5-difluorophenyl)aminocarbonylhydrazono]ethyl]pyridine-3-carboxylic acid (diflufenzopyr), N'-[3-chloro-4-(5-t-butyl-oxo-1,3,4-oxadiazol-3(2H)-yl)phenyl]-N,N-dimethylurea (dimefuron), S-(1-methyl-1-phenylethyl) 1-piperidinecarbothioate (dimepiperate), 2-chloro-N-(2,6-dimethylphenyl)-N-(2-methoxyethyl)acetamide (dimethachlor), N-(1,2-di-methylpropyl)-N'-ethyl-6-methylthio-1,3,5-triazine-2,4-diamine (dimethametryn), (S-) 2-chloro-N-(2,4-dimethyl-3-thienyl)-N-(2-methoxy-1-methylethyl)acetamide ((S-)(dimethenamid)), 2-amino-4-(1-fluoro-1-methylethyl)-6-(1-methyl-2-(3,5-dimethylphenoxy)ethylamino)-1,3,5-triazine (dimexyflam), 6,7-dihydrodipyrido[1,2-a:2',1'-c]pyrazinediium dibromide (diquat-dibromide), S,S-dimethyl 2-difluoromethyl-4-isobutyl-6-trifluoromethylpyridine-3,5-dicarbothioate (dithiopyr), N'-(3,4-dichlorophenyl)-N,N-di-methylurea (diuron), N-(4-methylphenyl)-N'-(1-methyl-1-phenylethyl)urea (dymron, daimuron), S-ethyl dipropylthiocarbamate (EPTC), S-(phenylmethyl) N-ethyl-N-(1,2-dimethylpropyl)thiocarbamate (Esprocarb), N-ethyl-N-(2-methyl-2-propenyl)-2,6-dinitro-4-trifluoromethylbenzeneamine (ethalfluralin), methyl 2-[[[[(4-ethoxy-6-methylamino-1,3,5-triazin-2-yl)amino]carbonyl]amino]sulphonyl]benzoate (ethametsulfuron-methyl), 2-ethoxy-2,3-dihydro-3,3-dimethyl-5-benzofuranylmethanesulphonate (ethofumesate), (S)-(2-ethoxy-1-methyl-2-oxoethyl) 2-chloro-5-(2-chloro-4-tri-fluoromethylphenoxy)benzoate (ethoxyfen), N-(4,6-dimethoxypyrimidin-2-yl)-N'-(2-ethoxyphenoxysulphonyl)urea (ethoxysulfuron), N-(2,3-dichlorophenyl)-4-ethoxymethoxybenzamide (etobenzanide), (R)-ethyl 2-[4-(6-chlorobenzoxazol-2-yloxy)phenoxy]propanoate (Fenoxaprop-(P)-ethyl), 4-(2-chlorophenyl)-N-cyclohexyl-N-ethyl-4,5-dihydro-5-oxo-1H-tetrazole-1-carboxamide (fentrazamide), isopropyl N-benzoyl-N-(3-chloro-4-fluorophenyl)-D-alaninate (flamprop-M-isopropyl), methyl N-benzoyl-N-(3-chloro-4-fluorophenyl)-D-alaninate (flamprop-M-methyl), N-[[(4,6-dimethoxy-2-pyrimidinyl)amino]carbonyl]-3-trifluoromethyl-2-pyridinesulphonamide (flazasulfuron), N-(2,6-difluorophenyl)-8-fluoro-5-methoxy-[1,2,4]-triazolo-[1,5-c]-pyrimidine-2-sulphonamide (florasulam), (R)-butyl 2-[4-(5-trifluoromethylpyridin-2-yloxy)phenoxy]propanoate (fluazifop-P-butyl), isopropyl 5-(4-bromo-1-methyl-5-trifluoromethyl-1H-pyrazol-3-yl)-2-chloro-4-fluorobenzoate (fluazolate), N-(4-fluorophenyl)-N-isopropyl-2-(5-trifluoromethyl-1,3,4-thiadiazol-2-yloxy)acetamide (flufenacet), ethyl[2-chloro-4-fluoro-5-(5-methyl-6-oxo-4-trifluoromethyl-1(6H)-pyridazinyl)phenoxy]-acetate (flufenpyr), N-(2,6-difluorophenyl)-5-methyl-1,2,4-triazolo[1,5-a]-pyrimidine-2-sulphonamide (flumetsulam), pentyl[2-chloro-4-fluoro-5-(1,3,4,5,6,7-hexahydro-1,3-dioxo-2H-isoindol-yl)phenoxy]acetate (flumiclorac-pentyl), 2-[7-fluoro-3,4-dihydro-3-oxo-4-(2-propynyl)-2H-1,4-benzoxazin-6-yl]-4,5,6,7-tetrahydro-1H-isoindole-1,3-dione (flumioxazin), 2-[4-chloro-2-fluoro-5-[(1-methyl-2-propynyl)oxy]phenyl]-4,5,6,7-tetrahydro-1H-isoindole-1,3(2H)-dione (flumipropyn), N,N-dimethyl-N'-(3-trifluoromethylphenyl)urea (fluometuron), 3-chloro-4-chloromethyl-1-(3-trifluoromethylphenyl)-2-pyrrolidinone (fluorochloridone), ethoxycarbonylmethyl 5-(2-chloro-4-trifluoromethylphenoxy)-2-nitrobenzoate (fluoroglyco-fen-ethyl), 1-(4-chloro-3-(2,2,3,3,3-pentafluoropropoxymethyl)phenyl)-5-phenyl-1H-1,2,4-triazol-3-carboxamide (flupoxam), 1-isopropyl-2-chloro-5-(3,6-dihydro-3-methyl-2,6-dioxo-4-trifluoromethyl-1(2H)-pyrimidyl)benzoate (flupropacil), N-(4,6-dimethoxypyrimidin-2-yl)-N'-(3-methoxycarbonyl-6-trifluoromethylpyridin-2-ylsulphonyl)urea sodium salt (flupyrsulfuron-methyl-sodium), 9-hydroxy-9H-fluorene-9-carboxylic acid (flurenol), (4-amino-3,5-dichloro-6-fluoropyridin-2-yloxy)acetic acid (2-butoxy-1-methylethyl ester, 1-methylheptyl ester) (fluoroxypyr, -butoxypropyl, -meptyl), 5-methylamino-2-phenyl-4-(3-trifluoromethylphenyl)-3(2H)-furanone (flurtamone), methyl[(2-chloro-4-fluoro-5-(tetrahydro-3-oxo-1H,3H-[1,3,4]-thiadiazolo-[3,4-a]-pyridazin-1-yliden)aminophenyl]thioacetate (fluthiacet-methyl), 5-(2-chloro-4-trifluoromethylphenoxy)-N-methylsulphonyl-2-nitrobenzamide (fomesafen), 2-[[[[(4,6-dimethoxy-2-pyrimidinyl)amino]carbonyl]amino]sulphonyl]-4-formylamino-N,N-dimethylbenzamide (foramsulfuron), 2-amino-4-(hydroxymethylphosphinyl)butanoic acid (ammonium salt) (glufosinate (ammonium)), N-phosphonomethylglycine (isopropylammonium salt) (glyphosate, isopropylammonium), methyl 3-chloro-5-[[[[(4,6-dimethoxy-2-pyrimidinyl)amino]carbonyl]amino]sulphonyl]-1-methyl-1H-pyrazole-4-carboxylate (halosulfuron-methyl), (R)-2-[4-(3-chloro-5-trifluoro-methylpyridin-2-yloxy)phenoxy]propanoic acid (methyl ester, 2-ethoxyethyl ester, butyl ester) (haloxyfop, -methyl, —P-methyl, -ethoxyethyl, -butyl), 3-cyclohexyl-6-dimethylamino-1-methyl-1,3,5-triazine-2,4(1H,3H)-dione (hexazinone), methyl 2-(4,5-dihydro-4-methyl-4-isopropyl-5-oxo-1H-imidazol-2-yl)-4-methylbenzoate (imazamethabenz-methyl), 2-(4,5-dihydro-4-methyl-4-isopropyl-5-oxo-1H-imidazol-2-yl)-5-methoxymethylpyridine-3-carboxylic acid (imazamox), 2-(4,5-dihydro-4-methyl-4-isopropyl-5-oxo-1H-imidazol-2-yl)-5-methylpyridine-3-carboxylic acid (imazapic), 2-(4,5-dihydro-4-methyl-4-(isopropyl)-5-oxo-1H-imidazol-2-yl)-3-pyridinecarboxylic acid (imazapyr), 2-(4,5-dihydro-4-methyl-4-isopropyl-5-oxo-1H-imidazol-2-yl)quinoline-3-carboxylic acid (imazaquin), 2-(4,5-dihydro-4-methyl-4-isopropyl-5-oxo-1H-imidazol-2-yl)-5-ethylpyridine-3-carboxylic acid (imazethapyr), N-(4,6-dimethoxypyrimidin-2-yl)-N'-(2-chloroimidazo[1,2-a]pyridin-3-ylsulphonyl)-urea (imazosulfuron), 2-[2-(3-chlorophenyl)oxiranylmethyl]-2-ethyl-1H-indene-1,3(2H)-dione (indanofan), N-(4-methoxy-6-methyl-1,3,5-triazin-2-yl)-N'-(5-iodo-2-methoxycarbonylphenylsulphonyl)urea sodium salt (iodo-sulfuron-methyl-sodium), 4-hydroxy-3,5-diiodobenzonitrile (ioxynil), N,N-di-methyl-N'-(4-isopropylphenyl)urea (isoproturon), N-(5-t-butyl-3-isoxazolyl)-N',N'-dimethylurea (isouron), N-(3-(1-ethyl-1-methylpropyl)isoxazol-5-yl)-2,6-dimethoxybenzamide (isoxaben), (4-chloro-2-methylsulphonylphenyl)-(5-cyclopropylisoxazol-4-yl)methanone (isoxachlortole), (5-cyclopropylisoxazol-4-yl)-(2-methylsulphonyl-4-trifluoromethylphenyl)methanone (isoxaflutole), 2-[(2,3-dihydro-5,8-dimethyl-1,1-dioxidospiro-[4H-1-benzothiopyran-4,2'-[1,3]-dioxolan-6-yl)carbonyl]-1,3-cyclohexanedione (ketospiradox), (2-ethoxy-1-methyl-2-oxoethyl) 5-(2-chloro-4-trifluoromethylphenoxy)-2-nitrobenzoate (lactofen), 3-cyclohexyl-6,7-dihydro-1H-cyclopenta-pyrimidine-2,4-(3H,5H)-dione (lenacil), N'-(3,4-dichlorophenyl)-N-methoxy-N-methylurea (linuron), (4-chloro-2-methylphenoxy)acetic acid (MCPA), (R)-2-(4-chloro-2-methylphenoxy)propionic acid (mecoprop-P), 2-(2-benzothiazol-yloxy)-N-methyl-N-phenyl-lacetamide (mefenacet), methyl 2-[[[[(4,6-dimethoxy-2-pyrimidinyl)amino]carbonyl]amino]sulphonyl]-4-[[(methylsulphonyl)amino]methyl]benzoate (mesosulfuron), 2-(4-methylsulphonyl-2-nitroben-zoyl)-1,3-cyclohexanedione (mesotrione), 4-amino-3-methyl-6-phenyl-1,2,4-triazin-5(4H)-one (metamitron), 2-chloro-N-(2,6-dimethylphenyl)-N-(1H-pyrazol-1-ylmethyl)acetamide (metazachlor), N-(2-benzothiazolyl)-N,N'-dimethylurea (methabenz-thiazuron), N'-(4-bromophenyl)-N-methoxy-N-methyl-lurea (metobromuron), (S)-2-chloro-N-(2-ethyl-6-me-thylphenyl)-N-(2-methoxy-1-methylethyl)acetamide (metolachlor, S-metolachlor), N-(2,6-dichloro-3-meth-ylphenyl)-5,7-dimethoxy-1,2,4-triazolo[1,5-a]-pyrimi-dine-2-sulphonamide (metosulam), N'-(3-chloro-4-methoxyphenyl)-N,N-dimethylurea (metoxuron), 4-amino-6-tert-butyl-3-methylthio-1,2,4-triazin-5(4H)-one (metribuzin), N-(4-methoxy-6-methyl-1,3,5-tri-azin-2-yl)-N'-(2-methoxycarbonylphenylsulphonyl) urea (metsulfuron-methyl), S-ethyl hexahydro-1H-azepine-1-carbothioate (molinate), 2-(2-naphthyloxy)-N-phenylpropanamide (naproanilide), N,N-diethyl-2-(1-naphthalenyloxy)propanamide (napropamide), N-butyl-N'-(3,4-di-chlorophenyl)-N-methylurea (nebu-ron), N-(4,6-dimethoxypyrimidin-2-yl)-N'-(3-dimeth-ylcarbamoylpyridin-2-ylsulphonyl)urea (nicosulfuron), 4-chloro-5-methylamino-2-(3-trifluoromethylphenyl)-3(2H)pyridazinone (norflurazon), S-(2-chlorobenzyl) N,N-diethylthiocarbamate (orbencarb), 4-dipropy-lamino-3,5-dinitrobenzenesulphonamide (oryzalin), 3-[2,4-dichloro-5-(2-propynyl-oxy)phenyl]-5-(t-bu-tyl)-1,3,4-oxadiazol-2(3H)-one (oxadiargyl), 3-[2,4-dichloro-5-(1-methylethoxy)phenyl]-5-(t-butyl)-1,3,4-oxadiazol-2(3H)-one (oxadiazon), N-(4,6-dimethylpyrimidin-2-yl)-N'-(2-oxetan-3-yl-oxycarb-onylphenylsulphonyl)urea (oxasulfuron), 3-[1-(3,5-dichlorophenyl)-1-isopropyl]-2,3-dihydro-6-methyl-5-phenyl-4H-1,3-oxazin-4-one (oxaziclomefone), 2-chloro-1-(3-ethoxy-4-nitrophenoxy)-4-trifluorom-ethylbenzene (oxyfluorfen), 1,1'-dimethyl-4,4'-bipyri-dinium (paraquat), 1-amino-N-(1-ethylpropyl)-3,4-dimethyl-2,6-dinitrobenzene (pendimethalin), 4-(t-butyl)-N-(1-ethylpropyl)-2,6-dinitrobenzenamine (pendralin), 2-(2,2-difluoroethoxy)-N-(5,8-dimethoxy [1,2,4]triazolo[1,5-c]pyrimidin-2-yl)-6-trifluoriometh-ylbenzenesulphonamide (penoxsulam), 3-(4-chloro-5-cyclopentyloxy-2-fluorophenyl)-5-(1-methylethylidene)-2,4-oxazolidinedione (pentoxazone), 2-chloro-N-(2-ethoxyethyl)-N-(2-me-thyl-1-phenyl-1-propenyl)acetamide (pethoxamid), O-methyl N-[3-(3-methylphenylaminocarbonyloxy) phenyl]carbamide (phenmedipham), 4-amino-3,5,6-trichloropyridine-2-carboxylic acid (picloram), N-(4-fluorophenyl)-6-(3-trifluoromethylphenoxy)pyridine-2-carboxamide (picolinafen), S-[2-(2-methyl-1-piperidinyl)-2-oxoethyl] O,O-picolinyl)-phosphorodithioate (piperophos), 2-chloro-N-(2,6-di-ethylphenyl)-N-(2-propoxyethyl)acetamide (preti-lachlor), N-(4,6-bis-difluoromethoxypyrimi-din-2-yl)-N'-(2-methoxycarbonylphenylsulphonyl)urea (primisulfuron-methyl), 1-chloro-N-[2-chloro-4-fluoro-5-[(6S,7aR)-6-fluorotetrahydro-1,3-dioxo-1H-pyrrolo[1,2-c]imidazol-2(3H)yl]phenyl]methane-sulphonamide (profluazol), 2-[1-[[2-(4-chlorophenoxy) propoxy]imino]butyl]-3-hydroxy-5-(tetrahydro-2H-thiopyranyl)-2-cyclohexen-1-one (profoxydim), N,N'-bis-isopropyl-6-methylthio-1,3,5-triazine-2,4-diamine (prometryn), 2-chloro-N-isopropyl-N-phenylacetamid (propachlor), N-(3,4-dichlorophenyl)propanamide (propanil), (R)-[2-[[(1-methylethylidene)amino]oxy] ethyl]2-[4-(6-chloro-2-quinoxalin-yloxy)phenoxy]pro-panoate (propaquizafop), 2-chloro-N-(2-ethyl-6-meth-ylphenyl)-N-[(1-methylethoxy)methyl]acetamide (propisochlor), methyl 2-[[[(4,5-dihydro-4-methyl-5-oxo-3-propoxy-1H-1,2,4-triazol-1-yl)carbonyl]amino] sulphonyl]benzoate sodium salt (propoxycarbazone-so-dium), 3,5-dichloro-N-(1,1-dimethyl-2-propynyl) benzamide (propyzamide), S-phenylmethyl N,N-dipropylthiocarbamate (prosulfocarb), N-(4-methoxy-6-methyl-1,3,5-triazin-2-yl)-N'-(2-(3,3,3-trifluoropropyl)phenylsulphonyl)urea (prosulfuron), 1-(3-chloro-4,5,6,7-tetrahydropyrazolo[1,5-a]pyridin-2-yl)-5-(methyl-2-propynylamino)-1H-pyrazol-4-car-bonitrile (pyraclonil), ethyl[2-chloro-5-(4-chloro-5-dif-luoromethoxy-1-methyl-1H-pyrazol-3-yl)-4-fluorophenoxy]acetate (pyraflufen-ethyl), 4-(2,4-dichlorobenzoyl)-1,3-dimethyl-5-(4-methylphenylsulphonyloxy)pyrazole (pyrazolate), N-(4,6-dimethoxypyrimidin-2-yl)-N'-(4-ethoxycarbo-nyl-1-methylpyrazol-5-ylsulphonyl)urea (pyr-azosulfu-ron-ethyl), 4-(2,4-dichlorobenzoyl)-1,3-dimethyl-5-(phenylcarbonyl-methoxy)pyrazole (pyrazoxyfen), diphenylmethanone 0-[2,6-bis-(4,6-di-methoxypyrimi-din-2-yl-oxy)benzoyl]oxime (pyribenzoxim), 0-[3-(1,1-dimethylethyl)phenyl] (6-methoxy-2-pyridinyl)me-thylthiocarbamate (pyributi-carb), 6-chloro-3-phenyl-4-pyridazinol (pyridafol), O-(6-chloro-3-phenylpyridazin-4-yl) S-octyl thiocarbonate (pyridate), 6-chloro-3-phenylpyridazin-4-ol (pyridatol), 7-[(4,6-dimethoxy-2-pyrimidinyl)thio]-3-methyl-1(3H)-isobenzofuranone (pyriftalid), methyl 2-(4,6-dimethoxypyrimidin-2-yloxy)benzoate (pyriminobac-methyl), 2-chloro-6-(4,6-dimethoxypyrimidin-2-ylthio)benzoic acid sodium salt (pyrithiobac-sodium), 3,7-di-chloroquinoline-8-carboxylic acid (quinchlo-rac), 7-chloro-3-methylquinoline-8-carboxylic acid (quinmerac), 2-amino-3-chloro-1,4-naphthalenedione (quinoclamine), (R)-2-[4-(6-chloro-2-quinoxalinyloxy) phenoxy]propanoic acid (ethyl ester, tetrahydro-2-fura-nylmethyl ester) (quizalofop, -ethyl, —P-ethyl, —P-tefuryl), N-(4,6-dimethoxypyrimidin-2-yl)-N'-(3-ethylsulphonylpyridin-2-yl-sulphonyl)urea (rimsulfu-ron), 2-(1-ethoximinobutyl)-5-(2-ethylthiopropyl)-3-hydroxy-2-cyclohexen-1-one (sethoxydim), 6-chloro-2,4-bis-ethylamino-1,3,5-triazine (simazine), 2-(2-chloro-4-methylsulphonylbenzoyl)cyclohexane-1,3-dione (sulcotrione), 2-(2,4-dichloro-5-methylsulphonylaminophenyl)-4-difluoromethyl-5-methyl-2,4-dihydro-3H-1,2,4-triazol-3-one (sulfentrazone), methyl 2-[[[[(4,6-dimethyl-2-pyrimidi-nyl)amino]carbonyl]amino]sulphonyl]benzoate (sulfo-meturon-methyl), N-phosphonomethylglycine trim-ethyl-sulphonium (sulfosate), N-(4,6-dimethoxypyrimidin-2-yl)-N'-(2-ethylsulphonyl) imidazo[1,2-a]pyridine-3-sulphonamide (sulfosulfuron), N-(5-t-butyl-1,3,4-thiadiazol-2-yl)-N, N'-dimethylurea (tebuthiuron), 2-[1-[(3-chloro-2-propenyl)oxyimino]propyl]-3-hydroxy-5-(tetrahydro-2H-pyran-4-yl)-2-cyclohexen-1-one (tepraloxydim), 6-chloro-4-ethylamino-2-t-butylamino-1,3,5-triazine (terbuthylazine), 2-t-butylamino-4-ethylamino-6-methylthio-1,3,5-triazine (terbutryn), 2-chloro-N-(2,6-dimethylphenyl)-N-(3-methoxy-2-thienylmethyl)acetamide (thenylchlor), 2-difluoromethyl-5-(4,5-dihydrothiazol-2-yl)-4-(2-methylpropyl)-6-trifluoromethylpyridine-3-carboxylate (thiazopyr), N-(4-methoxy-6-methyl-1,3,5-triazin-2-yl)-N'-(2-methoxycarbonylthien-3-ylsulphonyl)urea (thifensulfuron-methyl), S-phenylmethyl bis-s-butylcarbamothioate (tiocarbazil), 2-(ethoximinopropyl)-3-hydroxy-5-(2,4,6-trimethylphenyl)-2-cyclohexen-1-one (tralkoxydim), S-(2,3,3-trichloro-2-prop-enyl) diisopropylcarbamothioate (triallate), N-(4-methoxy-6-methyl-1,3,5-triazin-2-yl)-N'[2-(2-chloroethoxy)phenylsulphonyl]urea (triasulfuron), N-methyl-N-(4-methoxy-6-methyl-1,3,5-triazin-2-yl)-N'-(2-methoxycarb-onylphenylsulphonyl)urea (tribenuron-methyl), (3,5,6-trichloro)pyridin-2-yloxyacetic acid (triclopyr), 2-(3,5-dichlorophenyl)-2-(2,2,2-tri-chloroethyl)oxirane (tridiphane), N-[[(4,6-dimethoxy-2-pyrimi-dinyl)amino]carbonyl]-3-(2,2,2-trifluoroethoxy)-2-pyridinesulphonamide sodium salt (trifloxysulfuron), 1-amino-2,6-dinitro-N,N-dipropyl-4-trifluoro-methylbenzene (trifluralin), N-[4-dimethylamino-6-(2,2,2-trifluoroethoxy)-1,3,5-triazin-2-yl]-N'-(2-methoxycarbonylphenylsulphonyl)urea (triflusulfuron-methyl), N-(4-methoxy-6-trifluoromethoxy-1,3,5-triazin-2-yl)-N'-(2-tri-fluoromethylphenylsulphonyl)urea (tritosulfuron), N-[[(4,6-dimethoxy-2-pyri-midinyl)amino]carbonyl]-3-(N-methyl-N-methylsulphonylamino)-2-pyridinesulphonamide (cf. WO-A-91/10660), N-[[(4,6-dimethoxy-2-pyrimi-dinyl)amino]carbonyl]-3-(N-methyl-N-methylsulphonylamino)-2-pyridinesulphonamide (cf. WO-A-91/10660), 4-(4,5-dihydro-4-methyl-5-oxo-3-trifluoromethyl-1H-1,2,4-triazol-1-yl)-2-(ethylsulphonylamino)-5-fluorobenzenecarbothioamide (HWH4991, cf. WO-A-95/30661), 2-chloro-N-[1-(2,6-dichloro-4-difluoromethylphenyl)-4-nitro-1H-pyrazol-5-yl]propanecarboxamide (SLA5599, cf. EP-A-303153), [2-chloro-3-(4,5-dihydro-3-isoxazolyl)-4-methylsulphonylphenyl]-(5-hydroxy-1-methyl-1H-pyrazol-4-yl)methanone (cf. WO-A-96/26206, WO-A-98/31681), [3-(4,5-dihydro-3-isoxazolyl)-2-methyl-4-methylsulphonylphenyl]-(5-hydroxy-1-methyl-1H-pyrazol-4-yl)methanone (cf. WO-A-96/26206, WO-A-98/31681), [3-[2-chloro-3-[(2,6-dioxocyclohexyl)carbonyl]-6-ethylsulphonylphenyl]-5-isoxazolyl]acetonitrile (cf. WO-A-01/28341), 2-[2-chloro-4-methylsulphonyl-3-[(2,2,2-trifluoroethoxy)methyl]benzoyl]-1,3-cyclohexanedione (cf. WO-A-01/28341), 2-[[5,8-dimethyl-1,1-dioxido-4-(2-pyrimidinyloxy)-3,4-dihydro-2H-thiochromen-6-yl]carbonyl]-1,3-cyclohexanedione (cf. WO-A-01/28341)

("Active compounds of group 2"), and, if appropriate, definitely c) a compound that improves compatibility with crop plants, from the following group of compounds: 4-dichloroacetyl-1-oxa-4-azaspiro[4.5]decane (AD-67), 1-dichloroacetylhexa-hydro-3,3,8a-trimethylpyrrolo[1,2-a]pyrimidin-6(2H)-one (BAS-145138), 4-dichloroacetyl-3,4-dihydro-3-methyl-2H-1,4-benzoxazine (benoxacor), 1-methylhexyl 5-chloroquinoxalin-8-oxyacetate (cloquintocet-mexyl), α-(cyano-methoximino)phenylacetonitrile (cyometrinil), 2,4-dichlorophenoxyacetic acid (2,4-D), 2,2-dichloro-N-(2-oxo-2-(2-propenylamino)ethyl)-N-(2-propenyl)acetamide (DKA-24), 2,2-dichloro-N,N-di-2-propenylacetamide (dichlormid), N-(4-methylphenyl)-N'-(1-methyl-1-phenylethyl)urea (daimuron, dymron), 4,6-dichloro-2-phenylpyrimidine (fenclorim), 1-(2,4-dichlorophenyl)-5-trichloromethyl-1H-1,2,4-triazole-3-carboxylate (fenchlor-azol-ethyl), phenylmethyl 2-chloro-4-trifluoromethylthiazole-5-carboxylate (flurazole), 4-chloro-N-(1,3-dioxolan-2-ylmethoxy)-α-trifluoroacetophenone oxime (fluxofenim), 3-dichloroacetyl-5-(2-furanyl)-2,2-dimethyloxazolidine (furilazole, MON-13900), ethyl 4,5-dihydro-5,5-diphenyl-3-isoxazolcarb-oxylate (isoxadifen-ethyl), (4-chloro-2-methylphenoxy)acetic acid (MCPA), (+-)-2-(4-chloro-2-methylphenoxy)propanoic acid (mecoprop), diethyl 1-(2,4-dichlorophenyl)-4,5-dihydro-5-methyl-1H-pyrazol-3,5-dicarboxylate (mefen-pyr-diethyl), 2-dichloromethyl-2-methyl-1,3-dioxolane (MG-191), 1,8-naphthalic anhydride, α-(1,3-dioxolan-2-ylmethoximino)phenylacetonitrile (oxabetrinil), 2,2-dichloro-N-(1,3-dioxolan-2-ylmethyl)-N-(2-propenyl)acetamide (PPG-1292), 3-dichloroacetyl-2,2,5-trimethyloxazolidine (R-29148), N-cyclopropyl-4-[[(2-methoxy-5-methylbenzoyl)amino]sulphonyl]benzamide, N-[[(4-methoxyacetylamino)phenyl]sulphonyl]-2-methoxybenzamide and N-[[(4-methylaminocarbonylamino)phenyl]sulphonyl]-2-methoxybenzamide (the latter are in each case known from WO-A-99/66795)

("Active compounds of Group 3").

Preferred meanings of the groups listed above in connection with the formula (I) are defined below.

$Q^1$ preferably represents O (oxygen) or S (sulphur).

$Q^2$ preferably represents O (oxygen) or S (sulphur).

$R^1$ preferably represents in each case optionally cyano-, fluorine-, chlorine-, methoxy- or ethoxy-substituted methyl, ethyl, n- or isopropyl, n-, iso-, s- or t-butyl, represents in each case optionally cyano-, fluorine- or chlorine-substituted propenyl, butenyl, propynyl or butynyl, represents in each case optionally cyano-, fluorine-, chlorine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, represents in each case optionally cyano-, fluorine-, chlorine-, bromine-, methyl-, ethyl-, n- or isopropyl-, trifluoromethyl-, methoxy-, ethoxy-, n- or isopropoxy-, difluoromethoxy- or trifluoromethoxy-substituted phenyl, phenylmethyl or phenylethyl, or represents in each case optionally cyano-, fluorine-, chlorine-, bromine-, methyl-, ethyl-, n- or isopropyl-, methoxy-, ethoxy-, n- or isopropoxy-substituted heterocyclyl or heterocyclylmethyl, where the heterocyclyl group is in each case selected from the group consisting of oxetanyl, thietanyl, furyl, tetrahydrofuryl, thienyl and tetrahydro-thienyl.

$R^2$ preferably represents hydrogen, cyano, fluorine, chlorine, bromine, represents in each case optionally cyano-, fluorine-, chlorine-, methoxy- or ethoxy-substituted methyl, ethyl, n- or isopropyl, n-, iso-, s- or t-butyl, methoxy, ethoxy, n- or isopropoxy, methoxycarbonyl, ethoxycarbonyl, n- or isopropoxycarbonyl, methylthio, ethylthio, n- or isopropylthio, methylsulphinyl, ethylsulphinyl, methylsulphonyl or ethylsulphonyl, or represents in each case optionally cyano-, fluorine- or chlorine-substituted propenyl, butenyl, propynyl, butinyl, propenyloxy, butenyloxy, propinyloxy or butinyloxy.

$R^3$ preferably represents hydrogen, hydroxyl, mercapto, amino, cyano, fluorine, chlorine, bromine, or represents in each case optionally fluorine-, chlorine-, cyano-, methoxy-, ethoxy-, n- or isopropoxy-, acetyl-, propionyl-, n- or isobutyroyl-, methoxycarbonyl-, ethoxycarbonyl-, n- or isopropoxycarbonyl-substituted methyl, ethyl, n- or isopropyl, n-, iso-, s- or t-butyl, or represents in each case optionally fluorine-, chlorine-, and/or bromine-substituted ethenyl, propenyl, butenyl, ethynyl, propinyl or butinyl, represents in each case optionally fluorine-, chlorine-, cyano-, methoxy-, ethoxy-, n- or isopropoxy-, methoxycarbonyl-, ethoxycarbonyl-, n- or isopropoxycarbonyl-substituted methoxy, ethoxy, n- or isopropoxy, n-, iso-, s- or t-butoxy, methylthio, ethylthio, n- or isopropylthio, n-, iso-, s- or t-butylthio, methylamino, ethylamino, n- or isopropylamino, n-, iso-, s- or t-butyl-amino, acetylamino or propionylamino, or represents propenyloxy, butenyloxy, ethynyloxy, propinyloxy, butinyloxy, propenylthio, butenylthio, propinylthio, butinylthio, propenylamino, butenylamino, propinylamino or butinylamino, or represents dimethylamino, diethylamino or dipropylamino, represents in each case optionally fluorine-, chlorine-, methyl- and/or ethyl-substituted cyclopropyl, cyclobutyl, cyclopentyl, cyclohexyl, cyclopentenyl, cyclohexenyl, cyclopropyloxy, cyclobutyloxy, cyclopentyloxy, cyclohexyloxy, cyclopropylthio, cyclo-butylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexyl-methoxy, cyclopropylmethylthio, cyclobutylmethylthio, cyclopentyl-methylthio, cyclohexylmethylthio, cyclopropylmethylamino, cyclo-butylmethylamino, cyclopentylmethylamino or cyclohexylmethyl-amino, or represents in each case optionally fluorine-, chlorine-, bromine-, methyl-, trifluoromethyl-, methoxy- or methoxycarbonyl-substituted phenyl, benzyl, phenoxy, benzyloxy, phenylthio, benzyl-thio, phenylamino or benzylamino.

$R^4$ preferably represents hydrogen, hydroxyl, amino, or represents in each case optionally fluorine-, chlorine-, cyano-, methoxy- or ethoxy-substituted methyl, ethyl, n- or isopropyl, n-, iso-, s- or t-butyl, represents in each case optionally fluorine-, chlorine- and/or bromine-substituted ethenyl, propenyl, butenyl, propinyl or butinyl, represents in each case optionally fluorine-, chlorine-, cyano-, methoxy- or ethoxy-substituted methoxy, ethoxy, n- or isopropoxy, n-, iso-, s- or t-butoxy, methylamino, ethylamino, n- or isopropylamino, n-, iso-, s- or t-butylamino, represents propenyloxy or butenyloxy, represents di-methylamino or diethylamino, represents in each case optionally fluorine-, chlorine-methyl- and/ or ethyl-substituted cyclopropyl, cyclobutyl, cyclopentyl, cyclohexyl, cyclopropylamino, cyclobutyl-amino, cyclopentylamino, cyclohexylamino, cyclopropylmethyl, cyclobutylmethyl, cyclopentylmethyl or cyclohexylmethyl, or represents in each case optionally fluorine-, chlorine-, mtehyl-, trifluoromethyl- and/or methoxy-substituted phenyl or benzyl.

$R^3$ and $R^4$ together preferably represent trimethylene (propane-1,3-diyl), tetra-methylene (butane-1,4-diyl) or pentamethylene (pentane-1,5-diyl).

$Q^1$ particularly preferably represents O (oxygen).

$Q^2$ particularly preferably represents O (oxygen).

$R^1$ particularly preferably represents in each case optionally fluorine-, chlorine-, methoxy- or ethoxy-substituted methyl, ethyl, n- or isopropyl.

$R^2$ particularly preferably represents fluorine, chlorine, bromine or represents in each case optionally fluorine-, chlorine-, methoxy- or ethoxy-substituted methyl, ethyl, n- or isopropyl.

$R^3$ particularly preferably represents hydrogen, chlorine, bromine, or represents in each case optionally fluorine-, chlorine-, methoxy-, ethoxy-, n- or isopropoxy-substituted methyl, ethyl, n- or isopropyl, or represents in each case optionally fluorine- or chlorine-substituted ethenyl, propenyl, butenyl, propinyl or butynyl, or represents in each case optionally fluorine-, chlorine-, methoxy-, ethoxy-, n- or isopropoxy-substituted methoxy, ethoxy, n- or isopropoxy, methylthio, ethylthio, n- or isopropylthio, methylamino, ethylamino, n- or isopropylamino, represents propenyloxy, propynyloxy, propenylthio, propynylthio, propenylamino or propynylamino, represents dimethylamino or diethylamino, represents in each case optionally fluorine-, chlorine- or methyl-substituted cyclopropyl, cyclopropyloxy, cyclopropylmethyl or cyclopropylmethoxy, and $R^4$ particularly preferably represents in each case optionally fluorine-, chlorine-, methoxy- or ethoxy-substituted methyl, ethyl, n- or isopropyl, represents in each case optionally fluorine- or chlorine-substituted ethenyl, propenyl or propynyl, represents in each case optionally fluorine-, chlorine-, methoxy- or ethoxy-substituted methoxy, ethoxy, n- or isopropoxy, represents methylamino, or represents cyclopropyl.

Preferred active compound components of Group 1 are in particular also the sodium, potassium, magnesium, calcium, ammonium, $C_1$-$C_4$-alkylammonium, di-($C_1$-$C_4$-alkyl)ammonium, tri-($C_1$-$C_4$-alkyl)ammonium, tetra-($C_1$-$C_4$-alkyl)ammonium, tri-($C_1$-$C_4$-alkyl)sulphonium, $C_5$- or $C_6$-cycloalkylammonium and di-($C_1$-$C_2$-alkyl)benzylammonium salts of compounds of the formula (I) in which $Q^1$, $Q^2$, $R^1$, $R^2$, $R^3$ and $R^4$ have the meanings given above as being preferred.

Examples of compounds of the formula (I) which are very particularly preferred as active compound components according to the invention are listed in Table 1 below. The sodium salts of the compounds of Table 1, and in particular the sodium salts of the compounds I-1 and I-2, are likewise particularly emphasized as active compound components according to the invention.

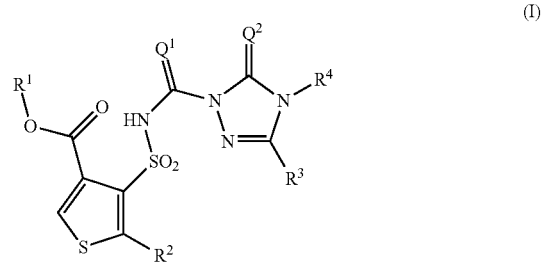

(I)

TABLE 1

Examples of compounds of the formula (I)

| Ex. No. | $Q^1$ | $Q^2$ | $R^1$ | $R^2$ | $R^3$ | $R^4$ | Melting point (° C.) |
|---|---|---|---|---|---|---|---|
| I-1 | O | O | $CH_3$ | $CH_3$ | $OC_2H_5$ | $CH_3$ | 163 |
| I-2 | O | O | $CH_3$ | $CH_3$ | $OCH_3$ | $CH_3$ | 201 |
| I-3 | O | O | $CH_3$ | $CH_3$ | $OC_3H_7$-n | $CH_3$ | 156 |
| I-4 | O | O | $CH_3$ | $CH_3$ | $OC_3H_7$-I | $CH_3$ | 150 |
| I-5 | O | O | $CH_3$ | $CH_3$ | $OCH_3$ |  | 218 |
| I-6 | O | O | $CH_3$ | $CH_3$ | $OC_2H_5$ |  | 170 |
| I-7 | O | O | $CH_3$ | $CH_3$ | $OC_3H_7$-n |  | 156 |
| I-8 | O | O | $CH_3$ | $CH_3$ | $OC_3H_7$-i |  | 188 |
| I-9 | O | O | $CH_3$ | $CH_3$ |  |  | 200 |
| I-10 | O | O | $CH_3$ | $CH_3$ | $CH_3$ | $CH_3$ | 178 |
| I-11 | O | O | $CH_3$ | $CH_3$ | $C_2H_5$ | $CH_3$ | 161 |
| I-12 | O | O | $CH_3$ | $CH_3$ | $SCH_3$ | $CH_3$ | 183 |

According to their chemical structure, the compounds of Group 2 can be assigned to the following classes of active compounds:

Amides (for example isoxaben, picolinafen, propanil), arylheterocycles (for example azafenidin, benzfendizone, butafenacil-allyl, carfentrazone-ethyl, cinidon-ethyl, fluazolate, flumiclorac-pentyl, flumioxazin, flupropacil, fluthiacet-methyl, oxadiazon, oxadiargyl, profluazol, pyraflufen-ethyl, pyridate, pyridafol, sulphentrazone, 4-[4,5-dihydro-4-methyl-5-oxo-(3-trifluoromethyl)-1H-1,2,4-triazol-1-yl]-2-[(ethylsulph-onyl)amino]-5-fluorobenzenecarbothioamide), aryloxyphenoxypropionate (for example clodinafop-propargyl, cyhalofop-butyl, diclofop-methyl, fenoxaprop-P-ethyl, fluazifop-P-butyl, haloxyfop-P-methyl, quizalofop-P-ethyl), carboxylic acid derivatives (for example clopyralid, dicamba, fluoroxypyr, picloram, triclopyr), benzo-thiadiazole (for example bentazone), chloroacetamides (for example acetochlor, alachlor, butachlor, (S-) dimethenamid, metazachlor, metolachlor, pretilachlor, propachlor, propisochlor), cyclohexanedione (for example butroxydim, clefoxydim, cycloxydim, sethoxydim, tralkoxydim), dinitroanilines (for example benfluralin, ethalfluralin, oryzalin, pendimethalin, trifluralin), diphenyl ethers (for example aci-fluorfen-sodium, aclonifen, bifenox, fluoroglycofen-ethyl, fomesafen, lactofen, oxyfluorfen), ureas (for example chlorotoluron, diuron, isoproturon, linuron, metobromuron, metoxuron), imidazolinones (for example imazamethabenz-methyl, imazamox, imazaquin, imazethapyr), isoxazole (for example isoxaflutole), nicotinanilides (for example diflufenican), nitriles (for example bromoxynil, ioxynil), organophosphorus compounds (for example anilofos, glufosinate-ammonium, glyphosate-isopropylammonium, sulphosate), oxyacetamides (for example flufenacet, mefenacet), phenoxycarboxylic acid derivatives (for example 2,4-D, dichloroprop-P, MCPA, MCPB, mecoprop), pyrazoles (for example pyrazolate, pyrazoxyfen), pyridazinones (for example norflurazon), pyridines (for example dithiopyr, thiazopyr), pyrimidinyl(thio)-benzoates (for example bispyribac, pyribenzoxim, pyrithiobac, pyriminobac), sulphonyl ureas (for example amidosulfuron, azimsulfuron, bensulfuron-methyl, chloroimuron-ethyl, chlorosulfuron, cinosulfuron, cyclosulfamuron, ethoxysulfuron, flupyrsulfuron-methyl-sodium, foramsulfuron, iodosulfuron-methyl-sodium, imazosulfuron, metsulfuron-methyl, nicosulfuron, oxasulfuron, primisulfuron-methyl, prosulfuron, pyrazosulfuron-ethyl, rimsulfuron, sulfometuron-methyl, sulfosulfuron, thi-fensulfuron-methyl, triasulfuron, tribenuron-methyl, trifloxysulfuron, triflusulfuron-methyl, tritosulfuron), tetrazolinones (for example fentrazamide), thiocarbamates (for example butylate, dimepiperate, EPTC, esprocarb, molinate, orbencarb, prosulfocarb, triallate), triazines (for example ametryn, atrazine, cyanazine, dimexyflam, simazine, terbuthylazine, terbutryn), triazinones (for example hexazinone, metamitron, metribuzin), triazoles (for example amitrole), triazolinones (for example amicarbazone, flu-carbazone-sodium, propoxycarbazone-sodium), triazolopyrimidines (for example cloransulam-methyl, diclosulam, florasulam, flumetsulam, metosulam), triketones (for example mesotrione, sulcotrione), uracils (for example bromacil).

Mixing components from the active compounds of the Group 2 which are particularly emphasized are: flucarbazone-sodium, acetochlor, aclonifen, alachlor, amicarbazone, amidosulfuron, amitrole, anilofos, asulam, atrazine, beflubutamid, benazolin (-ethyl), benfuresate, bentazone, bifenox, bispyribac-sodium, bromoxynil, butylate, carfentrazone-ethyl, chlorotoluron, chlorosulfuron, cinidon-ethyl, clodinafop-propargyl, clopyralid, cyanazine, 2,4-D, desmedipham, dicamba, dichlorprop-P, diclofop-methyl, difenzoquat, diflufenican, diflufenzopyr, dimethenamid, S-dimethenamid, EPTC, ethofumesate, ethoxysulfuron, fenoxaprop-ethyl, fenoxaprop-P-ethyl, fentrazamide, flamprop-M-isopropyl, flamprop-M-methyl, florasulam, fluazifop-P-butyl, fluazolate, flufenacet, flumetsulam, fluoroglycofen-ethyl, flupyrsulfuron-methyl-sodium, fluoroxypyr, -butoxypropyl, -meptyl, flurtamone, fluthiacet-methyl, foramsulfuron, glufosinate, glufosinate-ammonium, halosulfuron-methyl, haloxyfop-P-methyl, imazamethabenz-methyl, imazamox, imazapic, imazapyr, imazaquin, imazethapyr, iodosulfuron-methyl-sodium, ioxynil, isoproturon, isoxaben, isoxachlortole, isoxaflutole, lactofen, linuron, MCPA, mecoprop-P, mefenacet, mesosulfuron, mesotrione, metamitron, metazachlor, methabenzthiazuron, metolachlor, S-metolachlor, metosulam, metribuzin, metsulfuron-methyl, naproanilide, neburon, nicosulfuron, oxadiargyl, oxadiazon, ox-aziclomefone, oxyfluorfen, pendimethalin, penoxsulam, phenmedipham, picolinafen, primisulfuron-methyl, profluazol, propanil, propoxycarbazone-sodium, prosulfocarb, prosulfuron, pyraclonil, pyraflufen-ethyl, pyribenzoxim, pyridafol, pyridate, qin-clorac, quinmerac, rimsulfuron, sulcotrione, sulfosate, sulfosulfuron, terbuthylazine, thifensulfuron-methyl, tralkoxydim, triallate, triasulfuron, tribenuron-methyl, tritosulfuron, 4-(4,5-dihydro-4-methyl-5-oxo-3-trifluoromethyl-1H-1,2,4-triazol-1-yl)-2-(ethylsulphonylamino)-5-fluoro-benzenecarbothiamide (HWH4991), 2-chloro-N-[1-(2,6-dichloro-4-difluoromethylphenyl)-4-nitro-1H-pyrazol-5-yl]propanecarboxamide (SLA5599).

The compositions according to the invention preferably comprise one or two active compounds of Group 1, one to three active compounds of Group 2 and, if appropriate, one active compound of Group 3.

In particular, the compositions according to the invention comprise one active compound of Group 1, one or two active compounds of Group 2 and, if appropriate, one active compound of Group 3.

Examples of combinations according to the invention of in each case one active compound of Group 1 and one or two active compounds of Group 2—or of in each case one active compound of Group 1, one or two active compounds of Group 2 and one compound of Group 3—are listed below in Table 2. Here, the names of the active compounds of the formula (I) (active compounds of Group 1) are in each case taken from Table 1.

TABLE 2

Examples of combinations comprising one active compound of Group 1 and one or two active compounds of Group 2 (and, if appropriate, additionally a safener)

| Active compound from Group 1 | Active compound from Group 2 |
| --- | --- |
| (I-1) | aclonifen |
| (I-1) | amicarbazone |
| (I-1) | amidosulfuron |
| (I-1) | amitrole |
| (I-1) | anilofos |
| (I-1) | asulam |
| (I-1) | benazolin-ethyl |
| (I-1) | benfuresate |
| (I-1) | bifenox |
| (I-1) | bispyribac-sodium |
| (I-1) | bromoxynil |
| (I-1) | desmedipham |
| (I-1) | diclofop-methyl |
| (I-1) | diflufenican |
| (I-1) | ethofumesate |
| (I-1) | ethoxysulfuron |
| (I-1) | fenoxaprop-ethyl |
| (I-1) | fenoxaprop-P-ethyl |
| (I-1) | fentrazamide |
| (I-1) | fluazifop-P-butyl |
| (I-1) | fluazolate |
| (I-1) | flucarbazone-sodium |
| (I-1) | flufenacet |
| (I-1) | flurtamone |
| (I-1) | foramsulfuron |
| (I-1) | glufosinate |
| (I-1) | glufosinate-ammonium |
| (I-1) | iodosulfuron |
| (I-1) | ioxynil |
| (I-1) | isoproturon |
| (I-1) | isoxachlortole |
| (I-1) | isoxaflutole |
| (I-1) | lactofen |
| (I-1) | linuron |
| (I-1) | mefenacet |
| (I-1) | mesosulfuron |
| (I-1) | metamitron |
| (I-1) | methabenzthiazuron |
| (I-1) | metribuzin |
| (I-1) | neburon |
| (I-1) | oxadiargyl |
| (I-1) | oxadiazon |
| (I-1) | oxaziclomefone |
| (I-1) | phenmedipham |
| (I-1) | propanil |
| (I-1) | propoxycarbazone-sodium |
| (I-1) | pyraclonil |
| (I-1) | pyraflufen-ethyl |
| (I-1) | sulcotrione |
| (I-2) | aclonifen |
| (I-2) | amicarbazone |
| (I-2) | amidosulfuron |
| (I-2) | amitrole |
| (I-2) | anilofos |
| (I-2) | asulam |
| (I-2) | benazolin-ethyl |
| (I-2) | benfuresate |

TABLE 2-continued

Examples of combinations comprising one active compound of Group 1 and one or two active compounds of Group 2 (and, if appropriate, additionally a safener)

| Active compound from Group 1 | Active compound from Group 2 |
| --- | --- |
| (I-2) | bifenox |
| (I-2) | bispyribac-sodium |
| (I-2) | bromoxynil |
| (I-2) | desmedipham |
| (I-2) | diclofop-methyl |
| (I-2) | diflufenican |
| (I-2) | ethofumesate |
| (I-2) | ethoxysulfuron |
| (I-2) | fenoxaprop-ethyl |
| (I-2) | fenoxaprop-P-ethyl |
| (I-2) | fentrazamide |
| (I-2) | fluazifop-P-butyl |
| (I-2) | fluazolate |
| (I-2) | flucarbazone-sodium |
| (I-2) | flufenacet |
| (I-2) | flurtamone |
| (I-2) | foramsulfuron |
| (I-2) | glufosinate |
| (I-2) | glufosinate-ammonium |
| (I-2) | iodosulfuron |
| (I-2) | ioxynil |
| (I-2) | isoproturon |
| (I-2) | isoxachlortole |
| (I-2) | isoxaflutole |
| (I-2) | lactofen |
| (I-2) | linuron |
| (I-2) | mefenacet |
| (I-2) | mesosulfuron |
| (I-2) | metamitron |
| (I-2) | methabenzthiazuron |
| (I-2) | metribuzin |
| (I-2) | neburon |
| (I-2) | oxadiargyl |
| (I-2) | oxadiazon |
| (I-2) | oxaziclomefone |
| (I-2) | phenmedipham |
| (I-2) | propanil |
| (I-2) | propoxycarbazone-sodium |
| (I-2) | pyraclonil |
| (I-2) | pyraflufen-ethyl |
| (I-2) | sulcotrione |
| (I-3) | aclonifen |
| (I-3) | amicarbazone |
| (I-3) | amidosulfuron |
| (I-3) | amitrole |
| (I-3) | anilofos |
| (I-3) | asulam |
| (I-3) | benazolin-ethyl |
| (I-3) | benfuresate |
| (I-3) | bifenox |
| (I-3) | bispyribac-sodium |
| (I-3) | bromoxynil |
| (I-3) | desmedipham |
| (I-3) | diclofop-methyl |
| (I-3) | diflufenican |
| (I-3) | ethofumesate |
| (I-3) | ethoxysulfuron |
| (I-3) | fenoxaprop-ethyl |
| (I-3) | fenoxaprop-P-ethyl |
| (I-3) | fentrazamide |
| (I-3) | fluazifop-P-butyl |
| (I-3) | fluazolate |
| (I-3) | flucarbazone-sodium |
| (I-3) | flufenacet |
| (I-3) | flurtamone |
| (I-3) | foramsulfuron |
| (I-3) | glufosinate |
| (I-3) | glufosinate-ammonium |
| (I-3) | iodosulfuron |
| (I-3) | ioxynil |
| (I-3) | isoproturon |
| (I-3) | isoxachlortole |
| (I-3) | isoxaflutole |

TABLE 2-continued

Examples of combinations comprising one active compound of Group 1 and one or two active compounds of Group 2 (and, if appropriate, additionally a safener)

| Active compound from Group 1 | Active compound from Group 2 |
|---|---|
| (I-3) | lactofen |
| (I-3) | linuron |
| (I-3) | mefenacet |
| (I-3) | mesosulfuron |
| (I-3) | metamitron |
| (I-3) | methabenzthiazuron |
| (I-3) | metribuzin |
| (I-3) | neburon |
| (I-3) | oxadiargyl |
| (I-3) | oxadiazon |
| (I-3) | oxaziclomefone |
| (I-3) | phenmedipham |
| (I-3) | propanil |
| (I-3) | propoxycarbazone-sodium |
| (I-3) | pyraclonil |
| (I-3) | pyraflufen-ethyl |
| (I-3) | sulcotrione |
| (I-4) | aclonifen |
| (I-4) | amicarbazone |
| (I-4) | amidosulfuron |
| (I-4) | amitrole |
| (I-4) | anilofos |
| (I-4) | asulam |
| (I-4) | benazolin-ethyl |
| (I-4) | benfuresate |
| (I-4) | bifenox |
| (I-4) | bispyribac-sodium |
| (I-4) | bromoxynil |
| (I-4) | desmedipham |
| (I-4) | diclofop-methyl |
| (I-4) | diflufenican |
| (I-4) | ethofumesate |
| (I-4) | ethoxysulfuron |
| (I-4) | fenoxaprop-ethyl |
| (I-4) | fenoxaprop-P-ethyl |
| (I-4) | fentrazamide |
| (I-4) | fluazifop-P-butyl |
| (I-4) | fluazolate |
| (I-4) | flucarbazone-sodium |
| (I-4) | flufenacet |
| (I-4) | flurtamone |
| (I-4) | foramsulfuron |
| (I-4) | glufosinate |
| (I-4) | glufosinate-ammonium |
| (I-4) | iodosulfuron |
| (I-4) | ioxynil |
| (I-4) | isoproturon |
| (I-4) | isoxachlortole |
| (I-4) | isoxaflutole |
| (I-4) | lactofen |
| (I-4) | linuron |
| (I-4) | mefenacet |
| (I-4) | mesosulfuron |
| (I-4) | metamitron |
| (I-4) | methabenzthiazuron |
| (I-4) | metribuzin |
| (I-4) | neburon |
| (I-4) | oxadiargyl |
| (I-4) | oxadiazon |
| (I-4) | oxaziclomefone |
| (I-4) | phenmedipham |
| (I-4) | propanil |
| (I-4) | propoxycarbazone-sodium |
| (I-4) | pyraclonil |
| (I-4) | pyraflufen-ethyl |
| (I-4) | sulcotrione |
| (I-5) | aclonifen |
| (I-5) | amicarbazone |
| (I-5) | amidosulfuron |
| (I-5) | amitrole |
| (I-5) | anilofos |
| (I-5) | asulam |
| (I-5) | benazolin-ethyl |
| (I-5) | benfuresate |
| (I-5) | bifenox |
| (I-5) | bispyribac-sodium |
| (I-5) | bromoxynil |
| (I-5) | desmedipham |
| (I-5) | diclofop-methyl |
| (I-5) | diflufenican |
| (I-5) | ethofumesate |
| (I-5) | ethoxysulfuron |
| (I-5) | fenoxaprop-ethyl |
| (I-5) | fenoxaprop-P-ethyl |
| (I-5) | fentrazamide |
| (I-5) | fluazifop-P-butyl |
| (I-5) | fluazolate |
| (I-5) | flucarbazone-sodium |
| (I-5) | flufenacet |
| (I-5) | flurtamone |
| (I-5) | foramsulfuron |
| (I-5) | glufosinate |
| (I-5) | glufosinate-ammonium |
| (I-5) | iodosulfuron |
| (I-5) | ioxynil |
| (I-5) | isoproturon |
| (I-5) | isoxachlortole |
| (I-5) | isoxaflutole |
| (I-5) | lactofen |
| (I-5) | linuron |
| (I-5) | mefenacet |
| (I-5) | mesosulfuron |
| (I-5) | metamitron |
| (I-5) | methabenzthiazuron |
| (I-5) | metribuzin |
| (I-5) | neburon |
| (I-5) | oxadiargyl |
| (I-5) | oxadiazon |
| (I-5) | oxaziclomefone |
| (I-5) | phenmedipham |
| (I-5) | propanil |
| (I-5) | propoxycarbazone-sodium |
| (I-5) | pyraclonil |
| (I-5) | pyraflufen-ethyl |
| (I-5) | sulcotrione |
| (I-6) | aclonifen |
| (I-6) | amicarbazone |
| (I-6) | amidosulfuron |
| (I-6) | amitrole |
| (I-6) | anilofos |
| (I-6) | asulam |
| (I-6) | benazolin-ethyl |
| (I-6) | benfuresate |
| (I-6) | bifenox |
| (I-6) | bispyribac-sodium |
| (I-6) | bromoxynil |
| (I-6) | desmedipham |
| (I-6) | diclofop-methyl |
| (I-6) | diflufenican |
| (I-6) | ethofumesate |
| (I-6) | ethoxysulfuron |
| (I-6) | fenoxaprop-ethyl |
| (I-6) | fenoxaprop-P-ethyl |
| (I-6) | fentrazamide |
| (I-6) | fluazifop-P-butyl |
| (I-6) | fluazolate |
| (I-6) | flucarbazone-sodium |
| (I-6) | flufenacet |
| (I-6) | flurtamone |
| (I-6) | foramsulfuron |
| (I-6) | glufosinate |
| (I-6) | glufosinate-ammonium |
| (I-6) | iodosulfuron |
| (I-6) | ioxynil |
| (I-6) | isoproturon |
| (I-6) | isoxachlortole |

TABLE 2-continued

Examples of combinations comprising one active compound of Group 1 and one or two active compounds of Group 2 (and, if appropriate, additionally a safener)

| Active compound from Group 1 | Active compound from Group 2 |
|---|---|
| (I-6) | isoxaflutole |
| (I-6) | lactofen |
| (I-6) | linuron |
| (I-6) | mefenacet |
| (I-6) | mesosulfuron |
| (I-6) | metamitron |
| (I-6) | methabenzthiazuron |
| (I-6) | metribuzin |
| (I-6) | neburon |
| (I-6) | oxadiargyl |
| (I-6) | oxadiazon |
| (I-6) | oxaziclomefone |
| (I-6) | phenmedipham |
| (I-6) | propanil |
| (I-6) | propoxycarbazone-sodium |
| (I-6) | pyraclonil |
| (I-6) | praflufen-ethyl |
| (I-6) | sulcotrione |
| (I-7) | aclonifen |
| (I-7) | amicarbazone |
| (I-7) | amidosulfuron |
| (I-7) | amitrole |
| (I-7) | anilofos |
| (I-7) | asulam |
| (I-7) | benazolin-ethyl |
| (I-7) | benfuresate |
| (I-7) | bifenox |
| (I-7) | bispyribac-sodium |
| (I-7) | bromoxynil |
| (I-7) | desmedipham |
| (I-7) | diclofop-methyl |
| (I-7) | diflufenican |
| (I-7) | ethofumesate |
| (I-7) | ethoxysulfuron |
| (I-7) | fenoxaprop-ethyl |
| (I-7) | fenoxaprop-P-ethyl |
| (I-7) | fentrazamide |
| (I-7) | fluazifop-P-butyl |
| (I-7) | fluazolate |
| (I-7) | flucarbazone-sodium |
| (I-7) | flufenacet |
| (I-7) | flurtamone |
| (I-7) | foramsulfuron |
| (I-7) | glufosinate |
| (I-7) | glufosinate-ammonium |
| (I-7) | iodosulfuron |
| (I-7) | ioxynil |
| (I-7) | isoproturon |
| (I-7) | isoxachlortole |
| (I-7) | isoxaflutole |
| (I-7) | lactofen |
| (I-7) | linuron |
| (I-7) | mefenacet |
| (I-7) | mesosulfuron |
| (I-7) | metamitron |
| (I-7) | methabenzthiazuron |
| (I-7) | metribuzin |
| (I-7) | neburon |
| (I-7) | oxadiargyl |
| (I-7) | oxadiazon |
| (I-7) | oxaziclomefone |
| (I-7) | phenmedipham |
| (I-7) | propanil |
| (I-7) | propoxycarbazone-sodium |
| (I-7) | pyraclonil |
| (I-7) | pyraflufen-ethyl |
| (I-7) | sulcotrione |
| (I-8) | aclonifen |
| (I-8) | amicarbazone |
| (I-8) | amidosulfuron |
| (I-8) | amitrole |
| (I-8) | anilofos |
| (I-8) | asulam |
| (I-8) | benazolin-ethyl |
| (I-8) | benfuresate |
| (I-8) | bifenox |
| (I-8) | bispyribac-sodium |
| (I-8) | bromoxynil |
| (I-8) | desmedipham |
| (I-8) | diclofop-methyl |
| (I-8) | diflufenican |
| (I-8) | ethofumesate |
| (I-8) | ethoxysulfuron |
| (I-8) | fenoxaprop-ethyl |
| (I-8) | fenoxaprop-P-ethyl |
| (I-8) | fentrazamide |
| (I-8) | fluazifop-P-butyl |
| (I-8) | fluazolate |
| (I-8) | flucarbazone-sodium |
| (I-8) | flufenacet |
| (I-8) | flurtamone |
| (I-8) | foramsulfuron |
| (I-8) | glufosinate |
| (I-8) | glufosinate-ammonium |
| (I-8) | iodosulfuron |
| (I-8) | ioxynil |
| (I-8) | isoproturon |
| (I-8) | isoxachlortole |
| (I-8) | isoxaflutole |
| (I-8) | lactofen |
| (I-8) | linuron |
| (I-8) | mefenacet |
| (I-8) | mesosulfuron |
| (I-8) | metamitron |
| (I-8) | methabenzthiazuron |
| (I-8) | metribuzin |
| (I-8) | neburon |
| (I-8) | oxadiargyl |
| (I-8) | oxadiazon |
| (I-8) | oxaziclomefone |
| (I-8) | phenmedipham |
| (I-8) | propanil |
| (I-8) | propoxycarbazone-sodium |
| (I-8) | pyraclonil |
| (I-8) | pyraflufen-ethyl |
| (I-8) | sulcotrione |
| (I-9) | aclonifen |
| (I-9) | amicarbazone |
| (I-9) | amidosulfuron |
| (I-9) | amitrole |
| (I-9) | anilofos |
| (I-9) | asulam |
| (I-9) | benazolin-ethyl |
| (I-9) | benfuresate |
| (I-9) | bifenox |
| (I-9) | bispyribac-sodium |
| (I-9) | bromoxynil |
| (I-9) | desmedipham |
| (I-9) | diclofop-methyl |
| (I-9) | diflufenican |
| (I-9) | ethofumesate |
| (I-9) | ethoxysulfuron |
| (I-9) | fenoxaprop-ethyl |
| (I-9) | fenoxaprop-P-ethyl |
| (I-9) | fentrazamide |
| (I-9) | fluazifop-P-butyl |
| (I-9) | fluazolate |
| (I-9) | flucarbazone-sodium |
| (I-9) | flufenacet |
| (I-9) | flurtamone |
| (I-9) | foramsulfuron |
| (I-9) | glufosinate |
| (I-9) | glufosinate-ammonium |
| (I-9) | iodosulfuron |
| (I-9) | ioxynil |
| (I-9) | isoproturon |

TABLE 2-continued

Examples of combinations comprising one active compound of Group 1 and one or two active compounds of Group 2 (and, if appropriate, additionally a safener)

| Active compound from Group 1 | Active compound from Group 2 |
|---|---|
| (I-9) | isoxachlortole |
| (I-9) | isoxaflutole |
| (I-9) | lactofen |
| (I-9) | linuron |
| (I-9) | mefenacet |
| (I-9) | mesosulfuron |
| (I-9) | metamitron |
| (I-9) | methabenzthiazuron |
| (I-9) | metribuzin |
| (I-9) | neburon |
| (I-9) | oxadiargyl |
| (I-9) | oxadiazon |
| (I-9) | oxaziclomefone |
| (I-9) | phenmedipham |
| (I-9) | propanil |
| (I-9) | propoxycarbazone-sodium |
| (I-9) | pyraclonil |
| (I-9) | pyraflufen-ethyl |
| (I-9) | sulcotrione |
| (I-10) | aclonifen |
| (I-10) | amicarbazone |
| (I-10) | amidosulfuron |
| (I-10) | amitrole |
| (I-10) | anilofos |
| (I-10) | asulam |
| (I-10) | benazolin-ethyl |
| (I-10) | benfuresate |
| (I-10) | bifenox |
| (I-10) | bispyribac-sodium |
| (I-10) | bromoxynil |
| (I-10) | desmedipham |
| (I-10) | diclofop-methyl |
| (I-10) | diflufenican |
| (I-10) | ethofumesate |
| (I-10) | ethoxysulfuron |
| (I-10) | fenoxaprop-ethyl |
| (I-10) | fenoxaprop-P-ethyl |
| (I-10) | fentrazamide |
| (I-10) | fluazifop-P-butyl |
| (I-10) | fluazolate |
| (I-10) | flucarbazone-sodium |
| (I-10) | flufenacet |
| (I-10) | flurtamone |
| (I-10) | foramsulfuron |
| (I-10) | glufosinate |
| (I-10) | glufosinate-ammonium |
| (I-10) | iodosulfuron |
| (I-10) | ioxynil |
| (I-10) | isoproturon |
| (I-10) | isoxachlortole |
| (I-10) | isoxaflutole |
| (I-10) | lactofen |
| (I-10) | linuron |
| (I-10) | mefenacet |
| (I-10) | mesosulfuron |
| (I-10) | metamitron |
| (I-10) | methabenzthiazuron |
| (I-10) | metribuzin |
| (I-10) | neburon |
| (I-10) | oxadiargyl |
| (I-10) | oxadiazon |
| (I-10) | oxaziclomefone |
| (I-10) | phenmedipham |
| (I-10) | propanil |
| (I-10) | propoxycarbazone-sodium |
| (I-10) | pyraclonil |
| (I-10) | pyraflufen-ethyl |
| (I-10) | sulcotrione |
| (I-11) | aclonifen |
| (I-11) | amicarbazone |
| (I-11) | amidosulfuron |
| (I-11) | amitrole |
| (I-11) | anilofos |
| (I-11) | asulam |
| (I-11) | benazolin-ethyl |
| (I-11) | benfuresate |
| (I-11) | bifenox |
| (I-11) | bispyribac-sodium |
| (I-11) | bromoxynil |
| (I-11) | desmedipham |
| (I-11) | diclofop-methyl |
| (I-11) | diflufenican |
| (I-11) | ethofumesate |
| (I-11) | ethoxysulfuron |
| (I-11) | fenoxaprop-ethyl |
| (I-11) | fenoxaprop-P-ethyl |
| (I-11) | fentrazamide |
| (I-11) | fluazifop-P-butyl |
| (I-11) | fluazolate |
| (I-11) | flucarbazone-sodium |
| (I-11) | flufenacet |
| (I-11) | flurtamone |
| (I-11) | foramsulfuron |
| (I-11) | glufosinate |
| (I-11) | glufosinate-ammonium |
| (I-11) | iodosulfuron |
| (I-11) | ioxynil |
| (I-11) | isoproturon |
| (I-11) | isoxachlortole |
| (I-11) | isoxaflutole |
| (I-11) | lactofen |
| (I-11) | linuron |
| (I-11) | mefenacet |
| (I-11) | mesosulfuron |
| (I-11) | metamitron |
| (I-11) | methabenzthiazuron |
| (I-11) | metribuzin |
| (I-11) | neburon |
| (I-11) | oxadiargyl |
| (I-11) | oxadiazon |
| (I-11) | oxaziclomefone |
| (I-11) | phenmedipham |
| (I-11) | propanil |
| (I-11) | propoxycarbazone-sodium |
| (I-11) | pyraclonil |
| (I-11) | pyraflufen-ethyl |
| (I-11) | sulcotrione |
| (I-12) | aclonifen |
| (I-12) | amicarbazone |
| (I-12) | amidosulfuron |
| (I-12) | amitrole |
| (I-12) | anilofos |
| (I-12) | asulam |
| (I-12) | benazolin-ethyl |
| (I-12) | benfuresate |
| (I-12) | bifenox |
| (I-12) | bispyribac-sodium |
| (I-12) | bromoxynil |
| (I-12) | desmedipham |
| (I-12) | diclofop-methyl |
| (I-12) | diflufenican |
| (I-12) | ethofumesate |
| (I-12) | ethoxysulfuron |
| (I-12) | fenoxaprop-ethyl |
| (I-12) | fenoxaprop-P-ethyl |
| (I-12) | fentrazamide |
| (I-12) | fluazifop-P-butyl |
| (I-12) | fluazolate |
| (I-12) | flucarbazone-sodium |
| (I-12) | flufenacet |
| (I-12) | flurtamone |
| (I-12) | foramsulfuron |
| (I-12) | glufosinate |
| (I-12) | glufosinate-ammonium |
| (I-12) | iodosulfuron |
| (I-12) | ioxynil |

TABLE 2-continued

Examples of combinations comprising one active compound of Group 1 and one or two active compounds of Group 2 (and, if appropriate, additionally a safener)

| Active compound from Group 1 | Active compound from Group 2 |
|---|---|
| (I-12) | isoproturon |
| (I-12) | isoxachlortole |
| (I-12) | isoxaflutole |
| (I-12) | lactofen |
| (I-12) | linuron |
| (I-12) | mefenacet |
| (I-12) | mesosulfuron |
| (I-12) | metamitron |
| (I-12) | methabenzthiazuron |
| (I-12) | metribuzin |
| (I-12) | neburon |
| (I-12) | oxadiargyl |
| (I-12) | oxadiazon |
| (I-12) | oxaziclomefone |
| (I-12) | phenmedipham |
| (I-12) | propanil |
| (I-12) | propoxycarbazone-sodium |
| (I-12) | pyraclonil |
| (I-12) | pyraflufen-ethyl |
| (I-12) | sulcotrione |
| (I-1) | fenoxaprop-P-ethyl + mefenpyr-diethyl |
| (I-2) | fenoxaprop-P-ethyl + mefenpyr-diethyl |
| (I-3) | fenoxaprop-P-ethyl + mefenpyr-diethyl |
| (I-4) | fenoxaprop-P-ethyl + mefenpyr-diethyl |
| (I-5) | fenoxaprop-P-ethyl + mefenpyr-diethyl |
| (I-6) | fenoxaprop-P-ethyl + mefenpyr-diethyl |
| (I-7) | fenoxaprop-P-ethyl + mefenpyr-diethyl |
| (I-8) | fenoxaprop-P-ethyl + mefenpyr-diethyl |
| (I-9) | fenoxaprop-P-ethyl + mefenpyr-diethyl |
| (I-10) | fenoxaprop-P-ethyl + mefenpyr-diethyl |
| (I-11) | fenoxaprop-P-ethyl + mefenpyr-diethyl |
| (I-12) | fenoxaprop-P-ethyl + mefenpyr-diethyl |
| (I-1) | fenoxaprop-P-ethyl + isoxadifen-ethyl |
| (I-2) | fenoxaprop-P-ethyl + isoxadifen-ethyl |
| (I-3) | fenoxaprop-P-ethyl + isoxadifen-ethyl |
| (I-4) | fenoxaprop-P-ethyl + isoxadifen-ethyl |
| (I-5) | fenoxaprop-P-ethyl + isoxadifen-ethyl |
| (I-6) | fenoxaprop-P-ethyl + isoxadifen-ethyl |
| (I-7) | fenoxaprop-P-ethyl + isoxadifen-ethyl |
| (I-8) | fenoxaprop-P-ethyl + isoxadifen-ethyl |
| (I-9) | fenoxaprop-P-ethyl + isoxadifen-ethyl |
| (I-10) | fenoxaprop-P-ethyl + isoxadifen-ethyl |
| (I-11) | fenoxaprop-P-ethyl + isoxadifen-ethyl |
| (I-12) | fenoxaprop-P-ethyl + isoxadifen-ethyl |

Surprisingly, it has now been found that the above-defined active compound combinations of the substituted thien-3-yl-sulphonylamino(thio)carbonyltriazolin(ethi)-ones of the formula (I) and/or their salts and the abovementioned active compounds of Group 2 exhibit a particularly high herbicidal activity combined with very good crop plant compatibility and can be used for the selective control of monocotyledonous and dicotyledonous weeds in a variety of crops, in particular in cotton, barley, potatoes, maize, oilseed rape, rice, rye, soya beans, sunflowers, wheat, sugar cane and sugar beet, especially in barley, maize, rice and wheat, and additionally also for controlling monocotyledonous and dicotyledonous weeds in the semi- and nonselective field.

Surprisingly, the herbicidal activity of the active compound combinations according to the invention of compounds of the abovementioned Groups 1 and 2 exceeds the total of the action of the individual active compounds considerably.

Thus, not just a complementation of actions but a synergistic effect is present which could not have been predicted. The new active compound combinations are well tolerated in a variety of crops, also effecting good control of weeds which are usually difficult to control. Thus, the novel active compound combinations are a valuable addition to the herbicides.

The synergistic effect of the active compound combinations according to the invention is particularly strongly pronounced in certain concentration ratios. However, the weight ratios of the active compounds in the active compound combinations may be varied within relatively wide ranges. In general, from 0.001 to 1000 parts by weight, preferably from 0.002 to 500 parts by weight and particularly preferably from 0.01 to 100 parts by weight of active compound of Group 2 are used per part by weight of active compound of the formula (I).

The following may be particularly emphasised as mixing components from amongst the active compounds of Group 3: 1-methylhexyl 5-chloroquinoxalin-8-oxyacetate (cloquintocet-mexyl), ethyl 4,5-dihydro-5,5-diphenyl-3-isoxazole-carboxylate (isoxadifen-ethyl) and diethyl 1-(2,4-dichlorophenyl)-4,5-dihydro-5-methyl-1H-pyrazole-3,5-dicarboxylate (mefenpyr-diethyl), which are particularly suitable for improving the compatibility in barley and wheat and, to a certain extent, also in maize and rice, and 4-dichloroacetyl-1-oxa-4-azaspiro[4.5]-decane (AD-67), 1-dichloroacetyl-hexahydro-3,3,8a-trimethylpyrrolo[1,2-a]-pyrimidin-6(2H)-one (BAS-145138), 4-dichloroacetyl-3,4-dihydro-3-methyl-2H-1,4-benzoxazine (benoxacor), 2,2-dichloro-N,N-di-2-propenylacetamide (dichlormid), 3-dichloroacetyl-5-(2-furanyl)-2,2-dimethyloxazolidine (furilazole, MON-13900) and 3-dichloroacetyl-2,2,5-trimethyloxazolidine (R-29148), which are particularly suitable for improving the compatibility in maize.

It must be considered as surprising that, from amongst a multiplicity of known safeners or antidotes capable of antagonizing the harmful effects of a herbicide on the crop plants, it is precisely the abovementioned compounds of Group 3 which are capable of almost completely compensating the harmful effect, on the crop plants, of active compounds of the formula (I) and their salts, if appropriate also in combination with one or more of the abovementioned active compounds of Group 2, without adversely affecting the herbicidal efficacy towards the weeds.

Surprisingly, it has also been found that the herbicidally active substance 2,4-dichlorophenoxyacetic acid (2,4-D) and its derivatives, too, can play the safener role described above.

Accordingly, a preferred embodiment is also a mixture comprising a compound of the formula (I) and/or salts thereof on the one hand, and 2,4-D and/or its derivatives on the other hand, if appropriate in combination with one or more of the active compounds of Group 2 listed above. Typical derivatives of 2,4-D are, for example, its esters.

Surprisingly, it has also been found that the herbicidally active substances (4-chloro-2-methylphenoxy)acetic acid (MCPA) and (+-)-2-(4-chloro-2-methylphenoxy)propanoic acid (mecoprop) can also play a safener role. The compounds mentioned are described in the following patent applications: JP 63 072 605 and GB 00 820 180.

The compounds diethyl 1-(2,4-dichlorophenyl)-4,5-dihydro-5-methyl-1H-pyrazole-3,5-dicarboxylate (mefenpyr-diethyl), 1-methylhexyl[(5-chloro-8-quinolinyl)-oxy]acetate (cloquintocet-mexyl) and ethyl 1-(2,4-dichlorophenyl)-5-(trichloromethyl)-1H-1,2,4-triazole-3-carboxylate (fenchlorazole-ethyl) are described in the following patent applications: DE-A-39 39 503, EP-A-191 736 and DE-A-35 25 205. 2,4-D is a known herbicide.

The advantageous effect of the crop plant compatibility of the active compound combinations according to the invention is likewise particularly strongly pronounced at certain concentration ratios. However, the weight ratios of the active compounds in the active compound combinations can be varied within relatively wide ranges. In general, from 0.001 to 1000 parts by weight, preferably from 0.01 to 100 parts by weight and particularly preferably from 0.1 to 10 parts by weight of one of the crop plant compatibility-improving compounds mentioned above under (c) (antidotes/safeners) are used per part by weight of active compound of the formula (I) or its mixtures with active compounds of Group 2.

All plants and plant parts can be treated in accordance with the invention. Plants are to be understood as meaning in the present context all plants and plant populations such as desired and undesired wild plants or crop plants (inclusive of naturally occurring crop plants). Crop plants can be plants which can be obtained by conventional plant breeding and optimisation methods or by biotechnological and recombinant methods or by combinations of these methods, inclusive of the transgenic plants and inclusive of the plant varieties protectable or not protectable by plant breeders' rights. Plant parts are to be understood as meaning all aerial and subterranean plant parts and organs of the plants such as shoot, leaf, flower and root, examples which may be mentioned being leaves, needles, stalks, trunks, flowers, fruiting bodies, fruits, seeds, roots, tubers and rhizomes. The plant parts also include vegetative and generative propagation material, for example cuttings, tubers, rhizomes, seedlings and seeds.

The treatment according to the invention of the plant and plant parts with the active compounds is carried out directly or by allowing the compounds to act on their surroundings, environment or storage space by the customary treatment methods, for example by immersion, spraying, evaporation, fogging, scattering, painting on and, in the case of propagation material, in particular in the case of seeds, also by applying one or more coats.

Amongst the plants obtained by biotechnological and recombinant methods, or by combining these methods, plants which are emphasized are those which tolerate so-called ALS, 4-HPPD, EPSP and/or PPO inhibitors, such as, for example, Acuron plants.

The active compounds according to the invention can be used, for example, in the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compound combinations according to the invention is in no way restricted to these genera, but also extends in the same manner to other plants.

The active compound combinations to be used in accordance with the invention can be employed not only in conventional cultivation methods (suitably spaced row crops), in plantation crops (for example grapevines, fruit, citrus) and in industrial plants and railtracks, on paths and squares, but also for stubble treatment and in the minimum tillage method. They are furthermore suitable as dessicants (haulm killing in, for example, potatoes) or as defoliants (for example in cotton). They are furthermore suitable for use on non-crop areas. Other fields of application are nurseries, forests, grassland and the production of ornamentals.

The active compound combinations can be converted into the customary formulations such as solutions, emulsions, wettable powders, suspensions, powders, dusts, pastes, soluble powders, granules, suspo-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants and/or foam formers.

In the case of the use of water as an extender, organic solvents can, for example, also be used as cosolvents. The following are essentially suitable as liquid solvents: aromatics such as xylene, toluene, or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Solid carriers which are suitable are:
for example ammonium salts and ground natural minerals such as kaolins, clays, talc, chalk, quartz, attapulgite, montmorillonite or diatomaceous earth, and ground synthetic materials such as highly-dispersed silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compounds, preferably between 0.5 and 90%.

The active compound combinations according to the invention are generally applied in the form of ready mixes. However, the active compounds contained in the active compound combinations may also be applied in the form of individual formulations which are mixed upon use, that is, in the form of tank mixes.

The new active compound combinations, as such or in their formulations, may furthermore also be used as a mixture with other known herbicides, again with ready mixes or tank mixes being possible. A mixture with other known active compounds such as fungicides, insecticides, acaricides, nematicides, bird repellants, growth substances, plant nutrients and soil conditioners is also possible. It may furthermore be advantageous for specific applications, in particular for the post-emergence method, to incorporate into the formulations plant-tolerated mineral or vegetable oils (for example the commercial product "Rako Binol") or ammonium salts such as, for example, ammonium sulphate or ammonium thiocyanate, as further additives.

The new active compound combinations can be used as such, in the form of their formulations or the use forms which can be prepared from these formulations by further dilution, such as ready-to-use solutions, suspensions, emulsions, powders, pastes and granules. Application is effected in the customary manner, for example by pouring, spraying, atomizing, dusting or broadcasting.

The active compound combinations according to the invention can be applied before and after emergence of the plants, that is to say by the pre- and post-emergence method. They may also be incorporated into the soil prior to sowing.

The good herbicidal action of the new active compound combinations can be seen from the examples which follow. While the individual active compounds show weaknesses with regard to their herbicidal action, the combinations all show a very good herbicidal action which exceeds a simple sum of actions.

A synergistic effect in herbicides is always present when the herbicidal action of the active compound combination exceeds the action of the active compounds when applied individually.

The expected action for a given combination of two herbicides can be calculated as follows (cf. COLBY, S. R.: "Calculating synergistic and antagonistic responses of herbicide combinations", Weeds 15, pages 20-22, 1967):

If
$X$=% damage by herbicide A (active compound of the formula I) at an application rate of p kg/ha
and
$Y$=% damage by herbicide B (active compound of the formula II) at an application rate of q kg/ha
and
$E$=the expected damage of herbicides A+B at an application rate of p+q kg/ha,
then $$E = X + Y - (X*Y/100).$$

If the actual damage exceeds the calculated value, the combination has a superadditive effect, that is to say a synergistic effect.

The theoretically expected activity for a given combination of three herbicides can likewise be found in the literature mentioned above.

USE EXAMPLES

Example A

Post-Emergence Test/Greenhouse

Test plants are grown under control conditions (temperature and light). Once the plants have reached a height of 5 to 15 cm, the test compound or the combination of test compounds is applied by spraying such that the particular amounts of active compound desired are applied per unit area. The concentration of the spray liquor is chosen so that the particular amounts of active compound desired are applied in 500 liters of water/ha.

Following the spray application, the plant containers are kept in the greenhouse under constant light and temperature conditions.

After three weeks, the degree of damage to the plants is rated in % damage in comparison to the development of the untreated control.

The figures denote:
0%=no effect (like untreated control)
100%=total destruction Active compounds, application rates, test plants and results are shown in the tables below.

Here, a.i. denotes active ingredient (active compound).

TABLE A-1

| Active compound or active compound combination | Application rate(s) (g of a.i./ha) | Activity against *Chenopodium album* (%) | Calculated activity according to Colby (%) |
| --- | --- | --- | --- |
| (I-2) | 8 | 70 | |
| bromoxynil | 250 | 80 | |
| (I-2) + bromoxynil | 8 + 250 | 100 | 94 |

TABLE A-2

| Active compound or active compound combination | Application rate(s) (g of a.i./ha) | Activity against *Abutilon theophrasti* (%) | Calculated activity according to Colby (%) | Activity against *Xanthium strumarum* (%) | Calculated activity according to Colby (%) |
| --- | --- | --- | --- | --- | --- |
| (I-2) | 8 | 70 | | | |
| metosulam | 25 | 70 | | 90 | |
| metosulam | 12.5 | 60 | | 60 | |
| (I-2) + metosulam | 8 + 25 | 95 | 91 | 100 | 97 |
| (I-2) + metosulam | 8 + 12.5 | 95 | 88 | 100 | 88 |

TABLE A-1-1

| | Application rate g of ai/ha | Bromus secalinus observed | Bromus secalinus calculated* |
|---|---|---|---|
| I-2 | 15 | 70 | |
| | 4 | 70 | |
| flucarbazone-sodium | 60 | 70 | |
| I-2 + | 15 + 60 | 100 | 91 |
| flucarbazone-sodium | 4 + 60 | 100 | 91 |

TABLE A-1-2

| | Application rate g of ai/ha | Veronica persicaria observed | Veronica persicaria calculated* |
|---|---|---|---|
| I-2 | 15 | 60 | |
| flucarbazone-sodium | 60 | 60 | |
| | 30 | 20 | |
| I-2 + | 15 + 60 | 98 | 84 |
| flucarbazone-sodium | 15 + 30 | 80 | 68 |

*Values calculated according to Colby

TABLE A-1-3

| | Application rate g of ai/ha | Viola arvensis observed | Viola arvensis calculated* |
|---|---|---|---|
| I-2 | 8 | 50 | |
| | 4 | 40 | |
| flucarbazone-sodium | 15 | 30 | |
| I-2 + | 8 + 15 | 80 | 65 |
| flucarbazone-sodium | 4 + 15 | 80 | 58 |

TABLE A-1-4

| | Application rate g of ai/ha | Setaria viridis observed | Setaria viridis calculated* |
|---|---|---|---|
| I-2 | 8 | 90 | |
| | 4 | 80 | |
| amidosulfuron | 15 | 30 | |
| | 8 | 0 | |
| I-2 + | 8 + 15 | 98 | 93 |
| amidosulfuron | 4 + 15 | 98 | 86 |
| | 8 + 8 | 98 | 90 |
| | 4 + 8 | 95 | 80 |

*Values calculated according to Colby

TABLE A-1-5

| | Application rate | Avena fatua observed | Avena fatua calculated* |
|---|---|---|---|
| I-2 | 4 | 80 | |
| amidosulfuron | 15 | 0 | |
| | 8 | 0 | |
| I-2 + | 4 + 15 | 90 | 80 |
| amidosulfuron | 4 + 8 | 90 | 80 |

TABLE A-1-6

| | Application rate g of ai/ha | Bromus secalinus observed | Bromus secalinus calculated* |
|---|---|---|---|
| I-2 | 15 | 70 | |
| amidosulfuron | 8 | 0 | |
| I-2 + amidosulfuron | 15 + 8 | 90 | 70 |

*Values calculated according to Colby

TABLE A-1-7

| | Application rate g of ai/ha | Alopecurus myosuroides observed | Alopecurus myosuroides calculated* |
|---|---|---|---|
| I-2 | 15 | 90 | |
| | 8 | 90 | |
| | 4 | 70 | |
| carfentrazone-ethyl | 8 | 0 | |
| I-2 + | 15 + 8 | 98 | 90 |
| carfentrazone-ethyl | 8 + 8 | 95 | 90 |
| | 4 + 8 | 80 | 70 |

TABLE A-1-8

| | Application rate g of ai/ha | Cyperus esculentus observed | Cyperus esculentus calculated* |
|---|---|---|---|
| I-2 | 15 | 70 | |
| carfentrazone-ethyl | 8 | 30 | |
| | 4 | 0 | |
| I-2 + | 15 + 8 | 100 | 79 |
| carfentrazone-ethyl | 15 + 4 | 90 | 70 |

*Values calculated according to Colby

TABLE A-1-9

| | Application rate g of ai/ha | Chenopodium album observed | Chenopodium album calculated* |
|---|---|---|---|
| I-2 | 8 | 85 | |
| | 4 | 70 | |
| carfentrazone-ethyl | 8 | 50 | |
| | 4 | 30 | |
| | 2 | 0 | |
| I-2 + | 8 + 8 | 98 | 92.5 |
| carfentrazone-ethyl | 4 + 8 | 95 | 85 |
| | 8 + 4 | 98 | 89.5 |
| | 4 + 4 | 90 | 79 |
| | 8 + 2 | 98 | 85 |
| | 4 + 2 | 80 | 70 |

TABLE A-1-10

| | Application rate g of ai/ha | Alopecurus myosuroides observed | Alopecurus myosuroides calculated* |
|---|---|---|---|
| I-2 | 15 | 90 | |
| dicamba | 60 | 0 | |
| | 30 | 0 | |
| I-2 + | 15 + 60 | 98 | 90 |
| dicamba | 15 + 30 | 95 | 90 |

*Values calculated according to Colby

TABLE A-1-11

| | Application rate g of ai/ha | *Cyperus esculentus* observed | *Cyperus esculentus* calculated* |
|---|---|---|---|
| I-2 | 15 | 70 | |
| dicamba | 125 | 0 | |
| | 30 | 0 | |
| I-2 + | 15 + 125 | 95 | 70 |
| dicamba | 15 + 30 | 90 | 70 |

TABLE A-1-12

| | Application rate g of ai/ha | *Veronica persicaria* observed | *Veronica persicaria* calculated* |
|---|---|---|---|
| I-2 | 15 | 40 | |
| | 8 | 0 | |
| dicamba | 60 | 40 | |
| I-2 + | 15 + 60 | 80 | 64 |
| dicamba | 8 + 60 | 60 | 40 |

*Values calculated according to Colby

TABLE A-1-13

| | Application rate g of ai/ha | *Alopecurus myosuroides* observed | *Alopecurus myosuroides* calculated* |
|---|---|---|---|
| I-2 | 15 | 80 | |
| diflufenican | 125 | 70 | |
| | 60 | 50 | |
| | 30 | 50 | |
| I-2 + | 15 + 125 | 100 | 94 |
| diflufenican | 15 + 60 | 95 | 90 |
| | 15 + 30 | 95 | 90 |

TABLE A-1-14

| | Application rate g of ai/ha | *Avena fatua* observed | *Avena fatua* calculated* |
|---|---|---|---|
| I-2 | 15 | 70 | |
| | 8 | 70 | |
| | 4 | 70 | |
| diflufenican | 125 | 50 | |
| I-2 + | 15 + 125 | 95 | 85 |
| diflufenican | 8 + 125 | 95 | 85 |
| | 4 + 125 | 95 | 85 |

*Values calculated according to Colby

TABLE A-1-15

| | Application rate g of ai/ha | *Bromus secalinus* observed | *Bromus secalinus* calculated* |
|---|---|---|---|
| I-2 | 4 | 80 | |
| diflufenican | 30 | 10 | |
| I-2 + diflufenican | 4 + 30 | 95 | 82 |

TABLE A-1-16

| | Application rate g of ai/ha | *Alopecurus myosuroides* observed | *Alopecurus myosuroides* calculated* |
|---|---|---|---|
| I-2 | 15 | 80 | |
| | 8 | 80 | |
| dichlorprop-P | 250 | 20 | |
| | 125 | 0 | |
| | 60 | 0 | |
| I-2 + | 15 + 250 | 98 | 84 |
| dichlorprop-P | 8 + 250 | 98 | 84 |
| | 15 + 125 | 98 | 80 |
| | 8 + 125 | 95 | 80 |
| | 15 + 60 | 90 | 80 |
| | 8 + 60 | 90 | 80 |

*Values calculated according to Colby

TABLE A-1-17

| | Application rate g of ai/ha | *Avena fatua* observed | *Avena fatua* calculated* |
|---|---|---|---|
| I-2 | 15 | 70 | |
| | 8 | 70 | |
| | 4 | 70 | |
| dichlorprop-P | 250 | 10 | |
| | 125 | 0 | |
| I-2 + | 15 + 250 | 98 | 73 |
| dichlorprop-P | 8 + 250 | 98 | 73 |
| | 4 + 250 | 95 | 73 |
| | 15 + 125 | 95 | 70 |
| | 8 + 125 | 95 | 70 |
| | 4 + 125 | 95 | 70 |

*Values calculated according to Colby

TABLE A-1-18

| | Application rate g of ai/ha | *Matricaria inodora* observed | *Matricaria inodora* calculated* |
|---|---|---|---|
| I-2 | 15 | 95 | |
| | 4 | 70 | |
| dichlorprop-P | 250 | 0 | |
| | 125 | 0 | |
| | 60 | 0 | |
| I-2 + | 15 + 250 | 100 | 95 |
| dichlorprop-P | 4 + 250 | 95 | 70 |
| | 15 + 125 | 100 | 95 |
| | 4 + 125 | 90 | 70 |
| | 15 + 60 | 100 | 95 |
| | 4 + 60 | 90 | 70 |

TABLE A-1-19

| | Application rate g of ai/ha | *Bromus secalinus* observed | *Bromus secalinus* calculated* |
|---|---|---|---|
| I-2 | 8 | 80 | |
| | 4 | 70 | |
| | 2 | 70 | |
| bifenox | 250 | 10 | |
| | 125 | 0 | |
| | 60 | 0 | |
| I-2 + | 8 + 250 | 95 | 82 |
| bifenox | 4 + 250 | 90 | 73 |
| | 2 + 250 | 90 | 73 |
| | 8 + 125 | 95 | 80 |
| | 4 + 125 | 90 | 70 |
| | 2 + 125 | 90 | 70 |
| | 8 + 60 | 90 | 80 |

TABLE A-1-19-continued

| | Application rate g of ai/ha | Bromus secalinus observed | Bromus secalinus calculated* |
|---|---|---|---|
| | 4 + 60 | 90 | 70 |
| | 2 + 60 | 90 | 70 |

*Values calculated according to Colby

TABLE A-1-20

| | Application rate g of ai/ha | Avena fatua observed | Avena fatua calculated* |
|---|---|---|---|
| I-2 | 4 | 80 | |
| | 2 | 70 | |
| bifenox | 250 | 10 | |
| | 125 | 10 | |
| | 60 | 10 | |
| I-2 + | 4 + 250 | 90 | 82 |
| bifenox | 2 + 250 | 90 | 73 |
| | 4 + 125 | 90 | 82 |
| | 2 + 125 | 90 | 73 |
| | 4 + 60 | 90 | 82 |
| | 2 + 60 | 90 | 73 |

TABLE A-1-21

| | Application rate g of ai/ha | Xanthium strumarium observed | Xanthium strumarium calculated* |
|---|---|---|---|
| I-2 | 8 | 70 | |
| bifenox | 250 | 70 | |
| | 125 | 60 | |
| | 60 | 60 | |
| I-2 + | 8 + 250 | 98 | 91 |
| bifenox | 8 + 125 | 98 | 88 |
| | 8 + 60 | 98 | 88 |

*Values calculated according to Colby

TABLE A-1-22

| | Application rate g of ai/ha | Alopecurus myosuroides observed | Alopecurus myosuroides calculated* |
|---|---|---|---|
| I-2 | 4 | 80 | |
| | 2 | 70 | |
| 2,4-D ester | 250 | 0 | |
| | 125 | 0 | |
| I-2 + | 4 + 250 | 90 | 80 |
| 2,4-D ester | 2 + 250 | 90 | 70 |
| | 4 + 125 | 90 | 80 |
| | 2 + 125 | 90 | 70 |

*Values calculated according to Colby

TABLE A-1-23

| | Application rate g of ai/ha | Bromus secalinus observed | Bromus secalinus calculated* |
|---|---|---|---|
| I-2 | 8 | 80 | |
| | 4 | 70 | |
| | 2 | 70 | |
| 2,4-D ester | 250 | 0 | |
| | 125 | 0 | |
| | 60 | 0 | |
| I-2 + | 8 + 250 | 98 | 80 |
| 2,4-D ester | 4 + 250 | 90 | 70 |

TABLE A-1-23-continued

| | Application rate g of ai/ha | Bromus secalinus observed | Bromus secalinus calculated* |
|---|---|---|---|
| | 2 + 250 | 80 | 70 |
| | 8 + 125 | 98 | 80 |
| | 4 + 125 | 80 | 70 |
| | 2 + 125 | 80 | 70 |
| | 8 + 60 | 90 | 80 |
| | 4 + 60 | 80 | 70 |
| | 2 + 60 | 80 | 70 |

TABLE A-1-24

| | Application rate g of ai/ha | Cassia tora observed | Cassia tora calculated* |
|---|---|---|---|
| I-2 | 2 | 20 | |
| 2,4-D ester | 250 | 50 | |
| | 125 | 50 | |
| | 60 | 50 | |
| I-2 + | 2 + 250 | 80 | 60 |
| 2,4-D ester | 2 + 125 | 70 | 60 |
| | 2 + 60 | 70 | 60 |

*Values calculated according to Colby

TABLE A-1-25

| | Application rate g of ai/ha | Bromus secalinus observed | Bromus secalinus calculated* |
|---|---|---|---|
| I-2 | 2 | 90 | |
| fenoxaprop-(P)-ethyl | 30 | 0 | |
| | 15 | 0 | |
| | 8 | 0 | |
| I-2 + | 2 + 30 | 95 | 90 |
| fenoxaprop-(P)-ethyl | 2 + 15 | 95 | 90 |
| | 2 + 8 | 95 | 90 |

TABLE A-1-26

| | Application rate g of ai/ha | Ipomoea hederacea observed | Ipomoea hederacea calculated* |
|---|---|---|---|
| I-2 | 4 | 80 | |
| | 2 | 80 | |
| fenoxaprop-(P)-ethyl | 30 | 0 | |
| I-2 + | 4 + 30 | 90 | 80 |
| fenoxaprop-(P)-ethyl | 2 + 30 | 90 | 80 |

*Values calculated according to Colby

TABLE A-1-27

| | Application rate g of ai/ha | Veronica persicaria observed | Veronica persicaria calculated* |
|---|---|---|---|
| I-2 | 8 | 40 | |
| fenoxaprop-(P)-ethyl | 30 | 0 | |
| | 15 | 0 | |
| | 8 | 0 | |
| I-2 + | 8 + 30 | 98 | 40 |
| fenoxaprop-(P)-ethyl | 8 + 15 | 70 | 40 |
| | 8 + 8 | 70 | 40 |

TABLE A-1-28

| | Application rate g of ai/ha | Bromus secalinus observed | Bromus secalinus calculated* |
|---|---|---|---|
| I-2 | 8 | 80 | |
| | 4 | 80 | |
| flupyrsulfuron | 4 | 0 | |
| | 2 | 0 | |
| I-2 + | 8 + 4 | 95 | 80 |
| flupyrsulfuron | 4 + 4 | 90 | 80 |
| | 8 + 2 | 95 | 80 |
| | 4 + 2 | 90 | 80 |

*Values calculated according to Colby

TABLE A-1-29

| | Application rate g of ai/ha | Digitaria sanguinalis observed | Digitaria sanguinalis calculated* |
|---|---|---|---|
| I-2 | 8 | 80 | |
| | 4 | 60 | |
| | 2 | 30 | |
| flupyrsulfuron | 4 | 20 | |
| I-2 + | 8 + 4 | 99 | 84 |
| flupyrsulfuron | 4 + 4 | 80 | 68 |
| | 2 + 4 | 80 | 44 |

TABLE A-1-30

| | Application rate g of ai/ha | Polygonum convolvolus observed | Polygonum convolvolus calculated* |
|---|---|---|---|
| I-2 | 4 | 70 | |
| | 2 | 70 | |
| flupyrsulfuron | 4 | 80 | |
| | 2 | 70 | |
| I-2 + | 4 + 4 | 98 | 94 |
| flupyrsulfuron | 2 + 4 | 98 | 94 |
| | 4 + 2 | 98 | 91 |
| | 2 + 2 | 95 | 91 |

*Values calculated according to Colby

TABLE A-1-31

| | Application rate g of ai/ha | Bromus secalinus observed | Bromus secalinus calculated* |
|---|---|---|---|
| I-2 | 8 | 80 | |
| | 4 | 80 | |
| | 2 | 80 | |
| fluroxypyr | 125 | 0 | |
| | 60 | 0 | |
| I-2 + | 8 + 125 | 100 | 80 |
| fluroxypyr | 4 + 125 | 90 | 80 |
| | 2 + 125 | 90 | 80 |
| | 8 + 60 | 98 | 80 |
| | 4 + 60 | 90 | 80 |
| | 2 + 60 | 90 | 80 |

TABLE A-1-32

| | Application rate g of ai/ha | Matricaria inodora observed | Matricaria inodora calculated* |
|---|---|---|---|
| I-2 | 2 | 50 | |
| fluroxypyr | 125 | 70 | |
| | 60 | 30 | |

TABLE A-1-32-continued

| | Application rate g of ai/ha | Matricaria inodora observed | Matricaria inodora calculated* |
|---|---|---|---|
| I-2 + | 2 + 125 | 100 | 85 |
| fluroxypyr | 2 + 60 | 95 | 65 |

*Values calculated according to Colby

TABLE A-1-33

| | Application rate g of ai/ha | Veronica persicaria observed | Veronica persicaria calculated* |
|---|---|---|---|
| I-2 | 4 | 30 | |
| | 2 | 0 | |
| fluroxypyr | 125 | 90 | |
| I-2 + | 4 + 125 | 98 | 93 |
| fluroxypyr | 2 + 125 | 98 | 90 |

TABLE A-1-34

| | Application rate g of ai/ha | Bromus secalinus observed | Bromus secalinus calculated* |
|---|---|---|---|
| I-2 | 8 | 80 | |
| | 4 | 80 | |
| glyphosate | 250 | 80 | |
| | 125 | 20 | |
| I-2 + | 8 + 250 | 100 | 96 |
| glyphosate | 4 + 250 | 100 | 96 |
| | 8 + 125 | 98 | 84 |
| | 4 + 125 | 98 | 84 |

*Values calculated according to Colby

TABLE A-1-35

| | Application rate g of ai/ha | Eriochloa villosa observed | Eriochloa villosa calculated* |
|---|---|---|---|
| I-2 | 8 | 70 | |
| | 4 | 40 | |
| | 2 | 20 | |
| glyphosate | 250 | 70 | |
| I-2 + | 8 + 250 | 100 | 91 |
| glyphosate | 4 + 250 | 100 | 82 |
| | 2 + 250 | 95 | 76 |

TABLE A-1-36

| | Application rate g of ai/ha | Veronica persicaria observed | Veronica persicaria calculated* |
|---|---|---|---|
| I-2 | 4 | 30 | |
| | 2 | 0 | |
| glyphosate | 250 | 50 | |
| I-2 + | 4 + 250 | 100 | 65 |
| glyphosate | 2 + 250 | 100 | 50 |

*Values calculated according to Colby

TABLE A-1-37

| | Application rate g of ai/ha | Bromus secalinus observed | Bromus secalinus calculated* |
|---|---|---|---|
| I-2 | 8 | 80 | |
| | 4 | 80 | |
| imazamox | 8 | 60 | |
| I-2 + | 8 + 8 | 100 | 92 |
| imazamox | 4 + 8 | 100 | 92 |

TABLE A-1-38

| | Application rate g of ai/ha | Matricaria inodora observed | Matricaria inodora calculated* |
|---|---|---|---|
| I-2 | 2 | 50 | |
| imazamox | 15 | 50 | |
| | 8 | 30 | |
| I-2 + | 2 + 15 | 100 | 75 |
| imazamox | 2 + 8 | 100 | 65 |

*Values calculated according to Colby

TABLE A-1-39

| | Application rate g of ai/ha | Digitaria sanguinalis observed | Digitaria sanguinalis calculated* |
|---|---|---|---|
| I-2 | 8 | 80 | |
| | 4 | 60 | |
| | 2 | 30 | |
| imazamox | 8 | 30 | |
| I-2 + | 8 + 8 | 98 | 86 |
| imazamox | 4 + 8 | 98 | 72 |
| | 2 + 8 | 80 | 51 |

TABLE A-1-40

| | Application rate g of ai/ha | Bromus secalinus observed | Bromus secalinus calculated* |
|---|---|---|---|
| I-2 | 8 | 80 | |
| | 4 | 80 | |
| iodosulfuron | 4 | 0 | |
| | 2 | 0 | |
| I-2 + | 8 + 4 | 100 | 80 |
| iodosulfuron | 4 + 4 | 100 | 80 |
| | 8 + 2 | 98 | 80 |
| | 4 + 2 | 98 | 80 |

*Values calculated according to Colby

TABLE A-1-41

| | Application rate g of ai/ha | Veronica persicaria observed | Veronica persicaria calculated* |
|---|---|---|---|
| I-2 | 4 | 30 | |
| | 2 | 0 | |
| iodosulfuron | 2 | 90 | |
| I-2 + | 4 + 2 | 100 | 93 |
| iodosulfuron | 2 + 2 | 100 | 90 |

TABLE A-1-42

| | Application rate g of ai/ha | Setaria viridis observed | Setaria viridis calculated* |
|---|---|---|---|
| I-2 | 4 | 90 | |
| iodosulfuron | 4 | 0 | |
| | 2 | 0 | |
| I-2 + | 4 + 4 | 98 | 90 |
| iodosulfuron | 4 + 2 | 95 | 90 |

*Values calculated according to Colby

TABLE A-1-43

| | Application rate g of ai/ha | Bromus secalinus observed | Bromus secalinus calculated* |
|---|---|---|---|
| I-2 | 8 | 80 | |
| | 4 | 80 | |
| isoxaflutole | 4 | 0 | |
| | 2 | 0 | |
| I-2 + | 8 + 4 | 100 | 80 |
| isoxaflutole | 4 + 4 | 98 | 80 |
| | 8 + 2 | 100 | 80 |
| | 4 + 2 | 98 | 80 |

TABLE A-1-44

| | Application rate g of ai/ha | Alopecurus myosuroides observed | Alopecurus myosuroides calculated* |
|---|---|---|---|
| I-2 | 8 | 90 | |
| isoxaflutole | 4 | 0 | |
| | 2 | 0 | |
| I-2 + | 8 + 4 | 98 | 90 |
| isoxaflutole | 8 + 2 | 98 | 90 |

*Values calculated according to Colby

TABLE A-1-45

| | Application rate g of ai/ha | Matricaria inodora observed | Matricaria inodora calculated* |
|---|---|---|---|
| I-2 | 2 | 50 | |
| isoxaflutole | 4 | 70 | |
| I-2 + isoxaflutole | 2 + 4 | 100 | 85 |

TABLE A-1-46

| | Application rate g of ai/ha | Matricaria inodora observed | Matricaria inodora calculated* |
|---|---|---|---|
| I-2 | 2 | 50 | |
| mecoprop-P | 250 | 0 | |
| | 125 | 0 | |
| I-2 + | 2 + 250 | 100 | 50 |
| mecoprop-P | 2 + 125 | 98 | 50 |

*Values calculated according to Colby

TABLE A-1-47

|  | Application rate g of ai/ha | *Galium aparine* observed | *Galium aparine* calculated* |
|---|---|---|---|
| I-2 | 4 | 80 | |
| mecoprop-P | 250 | 40 | |
|  | 125 | 20 | |
| I-2 + | 4 + 250 | 98 | 88 |
| mecoprop-P | 4 + 125 | 95 | 84 |

TABLE A-1-48

|  | Application rate g of ai/ha | *Digitaria sanguinalis* observed | *Digitaria sanguinalis* calculated* |
|---|---|---|---|
| I-2 | 8 | 80 | |
| mecoprop-P | 250 | 70 | |
|  | 125 | 40 | |
| I-2 + | 8 + 250 | 100 | 94 |
| mecoprop-P | 8 + 125 | 98 | 88 |

*Values calculated according to Colby

TABLE A-1-49

|  | Application rate g of ai/ha | *Bromus secalinus* observed | *Bromus secalinus* calculated* |
|---|---|---|---|
| I-2 | 8 | 80 | |
|  | 4 | 80 | |
|  | 2 | 80 | |
| mesotrione | 30 | 0 | |
|  | 15 | 0 | |
| I-2 + | 8 + 30 | 100 | 80 |
| mesotrione | 4 + 30 | 98 | 80 |
|  | 2 + 30 | 95 | 80 |
|  | 8 + 15 | 99 | 80 |
|  | 4 + 15 | 98 | 80 |
|  | 2 + 15 | 95 | 80 |

TABLE A-1-50

|  | Application rate g of ai/ha | *Polygonum convolvolus* observed | *Polygonum convolvolus* calculated* |
|---|---|---|---|
| I-2 | 4 | 70 | |
|  | 2 | 70 | |
| mesotrione | 15 | 50 | |
| I-2 + | 4 + 15 | 98 | 85 |
| mesotrione | 2 + 15 | 95 | 85 |

*Values calculated according to Colby

TABLE A-1-51

|  | Application rate g of ai/ha | *Alopecurus myosuroides* observed | *Alopecurus myosuroides* calculated* |
|---|---|---|---|
| I-2 | 8 | 90 | |
|  | 2 | 70 | |
| mesotrione | 30 | 0 | |
|  | 15 | 0 | |
| I-2 + | 8 + 30 | 95 | 90 |
| mesotrione | 2 + 30 | 95 | 70 |
|  | 8 + 15 | 95 | 90 |
|  | 2 + 15 | 80 | 70 |

TABLE A-1-52

|  | Application rate g of ai/ha | *Cassia tora* observed | *Cassia tora* calculated* |
|---|---|---|---|
| I-2 | 8 | 0 | |
| florasulam | 4 | 0 | |
| I-2 + | 8 + 4 | 98 | 0 |
| florasulam | | | |

*Values calculated according to Colby

TABLE A-1-53

|  | Application rate g of ai/ha | *Bromus secalinus* observed | *Bromus secalinus* calculated* |
|---|---|---|---|
| I-2 | 2 | 70 | |
| florasulam | 4 | 30 | |
|  | 2 | 30 | |
| I-2 + | 2 + 4 | 95 | 79 |
| florasulam | 2 + 2 | 95 | 79 |

TABLE A-1-54

|  | Application rate g of ai/ha | *Veronica persicaria* observed | *Veronica persicaria* calculated* |
|---|---|---|---|
| I-2 | 8 | 0 | |
| florasulam | 4 | 70 | |
| I-2 + | 8 + 4 | 98 | 70 |
| florasulam | | | |

*Values calculated according to Colby

TABLE A-1-55

|  | Application rate g of ai/ha | *Ipomoea hederacea* observed | *Ipomoea hederacea* calculated* |
|---|---|---|---|
| I-2 | 8 | 80 | |
| foramsulfuron | 15 | 80 | |
| I-2 + | 8 + 15 | 100 | 96 |
| foramsulfuron | | | |

TABLE A-1-56

|  | Application rate g of ai/ha | *Cyperus esculentus* observed | *Cyperus esculentus* calculated* |
|---|---|---|---|
| I-2 | 4 | 20 | |
| foramsulfuron | 8 | 80 | |
| I-2 + | 4 + 8 | 90 | 84 |
| foramsulfuron | | | |

*Values calculated according to Colby

TABLE A-1-57

|  | Application rate g of ai/ha | *Eriochloa villosa* observed | *Eriochloa villosa* calculated* |
|---|---|---|---|
| I-2 | 4 | 40 | |
|  | 2 | 0 | |
| foramsulfuron | 15 | 60 | |
| I-2 + | 4 + 15 | 80 | 76 |
| foramsulfuron | 2 + 15 | 70 | 60 |

TABLE A-1-58

| | Application rate g of ai/ha | Bromus secalinus observed | Bromus secalinus calculated* |
|---|---|---|---|
| I-2 | 2 | 70 | |
| flurtamone | 60 | 30 | |
| I-2 + flurtamone | 2 + 60 | 95 | 79 |

*Values calculated according to Colby

TABLE A-1-59

| | Application rate g of ai/ha | Matricaria inodora observed | Matricaria inodora calculated* |
|---|---|---|---|
| I-2 | 2 | 80 | |
| flurtamone | 30 | 30 | |
| I-2 + flurtamone | 2 + 30 | 95 | 86 |

TABLE A-1-60

| | Application rate g of ai/ha | Cyperus esculentus observed | Cyperus esculentus calculated* |
|---|---|---|---|
| I-2 | 4 | 20 | |
| | 2 | 0 | |
| mesosulfuron | 15 | 70 | |
| | 8 | 70 | |
| I-2 + mesosulfuron | 4 + 15 | 90 | 76 |
| | 2 + 15 | 90 | 70 |
| | 4 + 8 | 90 | 76 |
| | 2 + 8 | 90 | 70 |

*Values calculated according to Colby

TABLE A-1-61

| | Application rate g of ai/ha | Bromus secalinus observed | Bromus secalinus calculated* |
|---|---|---|---|
| I-2 | 2 | 70 | |
| mesosulfuron | 8 | 0 | |
| I-2 + mesosulfuron | 2 + 8 | 90 | 70 |

TABLE A-1-62

| | Application rate g of ai/ha | Avena fatua observed | Avena fatua calculated* |
|---|---|---|---|
| I-2 | 8 | 90 | |
| | 4 | 90 | |
| | 2 | 50 | |
| metosulam | 8 | 0 | |
| I-2 + metosulam | 8 + 8 | 98 | 90 |
| | 4 + 8 | 95 | 90 |
| | 2 + 8 | 90 | 50 |

*Values calculated according to Colby

TABLE A-1-63

| | Application rate g of ai/ha | Veronica persicaria observed | Veronica persicaria calculated* |
|---|---|---|---|
| I-2 | 8 | 0 | |
| | 4 | 0 | |
| metosulam | 4 | 80 | |
| I-2 + Metosulam | 8 + 4 | 100 | 80 |
| | 4 + 4 | 100 | 80 |

TABLE A-1-64

| | Application rate g of ai/ha | Digitaria sanguinalis observed | Digitaria sanguinalis calculated* |
|---|---|---|---|
| I-2 | 2 | 70 | |
| metosulam | 8 | 30 | |
| I-2 + metosulam | 2 + 8 | 90 | 79 |

*Values calculated according to Colby

TABLE A-1-65

| | Application rate g of ai/ha | Matricaria inodora observed | Matricaria inodora calculated* |
|---|---|---|---|
| I-2 | 2 | 80 | |
| metribuzin | 30 | 0 | |
| I-2 + metribuzin | 2 + 30 | 95 | 80 |

TABLE A-1-66

| | Application rate g of ai/ha | Xanthium strumarium observed | Xanthium strumarium calculated* |
|---|---|---|---|
| I-2 | 4 | 90 | |
| metribuzin | 30 | 40 | |
| I-2 + metribuzin | 4 + 30 | 98 | 94 |

*Values calculated according to Colby

TABLE A-1-67

| | Application rate g of ai/ha | Lolium perenne observed | Lolium perenne calculated* |
|---|---|---|---|
| I-2 | 2 | 70 | |
| metsulfuron | 2 | 70 | |
| I-2 + metsulfuron | 2 + 2 | 100 | 91 |

TABLE A-1-68

| | Application rate g of ai/ha | Bromus secalinus observed | Bromus secalinus calculated* |
|---|---|---|---|
| I-2 | 2 | 80 | |
| metsulfuron | 4 | 0 | |
| | 2 | 0 | |
| I-2 + metsulfuron | 2 + 4 | 95 | 80 |
| | 2 + 2 | 95 | 80 |

TABLE A-1-68-continued

| Application rate g of ai/ha | Bromus secalinus observed | Bromus secalinus calculated* |
|---|---|---|

*Values calculated according to Colby

TABLE A-1-69

| | Application rate g of ai/ha | Cyperus esculentus observed | Cyperus esculentus calculated* |
|---|---|---|---|
| I-2 | 8 | 80 | |
| | 4 | 60 | |
| | 2 | 40 | |
| metsulfuron | 4 | 30 | |
| I-2 + | 8 + 4 | 95 | 86 |
| metsulfuron | 4 + 4 | 90 | 72 |
| | 2 + 4 | 80 | 58 |

TABLE A-1-70

| | Application rate g of ai/ha | Eriochloa villosa observed | Eriochloa villosa calculated* |
|---|---|---|---|
| I-2 | 2 | 0 | |
| nicosulfuron | 30 | 90 | |
| I-2 + nicosulfuron | 2 + 30 | 95 | 90 |

*Values calculated according to Colby

TABLE A-1-71

| | Application rate g of ai/ha | Eriochloa villosa observed | Eriochloa villosa calculated* |
|---|---|---|---|
| I-2 | 8 | 60 | |
| | 4 | 30 | |
| | 2 | 0 | |
| picolinafen | 30 | 80 | |
| | 15 | 30 | |
| I-2 + | 8 + 30 | 98 | 92 |
| picolinafen | 4 + 30 | 95 | 86 |
| | 2 + 30 | 90 | 80 |
| | 8 + 15 | 95 | 72 |
| | 4 + 15 | 90 | 51 |
| | 2 + 15 | 90 | 30 |

TABLE A-1-72

| | Application rate g of ai/ha | Lolium perenne observed | Lolium perenne calculated* |
|---|---|---|---|
| I-2 | 2 | 70 | |
| picolinafen | 30 | 20 | |
| | 15 | 0 | |
| I-2 + | 2 + 30 | 95 | 76 |
| picolinafen | 2 + 15 | 95 | 70 |

*Values calculated according to Colby

TABLE A-1-73

| | Application rate g of ai/ha | Cassia tora observed | Cassia tora calculated* |
|---|---|---|---|
| I-2 | 8 | 0 | |
| | 4 | 0 | |
| picolinafen | 30 | 70 | |
| I-2 + | 8 + 30 | 100 | 70 |
| picolinafen | 4 + 30 | 80 | 70 |

TABLE A-1-74

| | Application rate g of ai/ha | Veronica persicaria observed | Veronica persicaria calculated* |
|---|---|---|---|
| I-2 | 4 | 0 | |
| propoxycarbazone-sodium | 60 | 40 | |
| I-2 + propoxycarbazone-sodium | 4 + 60 | 100 | 40 |

*Values calculated according to Colby

TABLE A-1-75

| | Application rate g of ai/ha | Cassia tora observed | Cassia tora calculated* |
|---|---|---|---|
| I-2 | 8 | 0 | |
| | 4 | 0 | |
| propoxycarbazone-sodium | 30 | 30 | |
| I-2 + | 8 + 30 | 80 | 30 |
| propoxycarbazone-sodium | 4 + 30 | 70 | 30 |

TABLE A-1-76

| | Application rate g of ai/ha | Polygonum convolvolus observed | Polygonum convolvolus calculated* |
|---|---|---|---|
| I-2 | 4 | 80 | |
| | 2 | 70 | |
| propoxycarbazone-sodium | 60 | 0 | |
| | 30 | 0 | |
| I-2 + | 4 + 60 | 90 | 80 |
| propoxycarbazone-sodium | 2 + 60 | 90 | 70 |
| | 4 + 30 | 90 | 80 |
| | 2 + 30 | 90 | 70 |

*Values calculated according to Colby

TABLE A-1-77

| | Application rate g of ai/ha | Cassia tora observed | Cassia tora calculated* |
|---|---|---|---|
| I-2 | 8 | 0 | |
| rimsulfuron | 8 | 80 | |
| | 4 | 60 | |
| I-2 + | 8 + 8 | 100 | 80 |
| rimsulfuron | 8 + 4 | 80 | 60 |

TABLE A-1-78

|  | Application rate g of ai/ha | Abutilon theophrasti observed | Abutilon theophrasti calculated* |
|---|---|---|---|
| I-2 | 4 | 70 |  |
|  | 2 | 60 |  |
| rimsulfuron | 4 | 70 |  |
| I-2 + | 4 + 4 | 95 | 91 |
| rimsulfuron | 2 + 4 | 95 | 88 |

*Values calculated according to Colby

TABLE A-1-79

|  | Application rate g of ai/ha | Avena fatua observed | Avena fatua calculated* |
|---|---|---|---|
| I-2 | 2 | 70 |  |
| rimsulfuron | 8 | 70 |  |
|  | 4 | 70 |  |
| I-2 + | 2 + 8 | 95 | 91 |
| rimsulfuron | 2 + 4 | 95 | 91 |

TABLE A-1-80

|  | Application rate g of ai/ha | Bromus secalinus observed | Bromus secalinus calculated* |
|---|---|---|---|
| I-2 | 8 | 80 |  |
|  | 4 | 70 |  |
| sulcotrione | 120 | 30 |  |
|  | 60 | 0 |  |
| I-2 + | 8 + 120 | 98 | 86 |
| sulcotrione | 4 + 120 | 90 | 79 |
|  | 8 + 60 | 98 | 80 |
|  | 4 + 60 | 90 | 70 |

*Values calculated according to Colby

TABLE A-1-81

|  | Application rate g of ai/ha | Bromus secalinus observed | Bromus secalinus calculated* |
|---|---|---|---|
| I-2 | 8 | 80 |  |
|  | 4 | 70 |  |
|  | 2 | 70 |  |
| terbuthylazine | 500 | 50 |  |
| I-2 + | 8 + 500 | 100 | 90 |
| terbuthylazine | 4 + 500 | 100 | 85 |
|  | 2 + 500 | 100 | 85 |

TABLE A-1-82

|  | Application rate g of ai/ha | Setaria viridis observed | Setaria viridis calculated* |
|---|---|---|---|
| I-2 | 8 | 95 |  |
| thifensulfuron-methyl | 15 | 0 |  |
|  | 8 |  |  |
| I-2 + | 8 + 15 | 100 | 95 |
| thifensulfuron-methyl | 8 + 8 | 100 | 95 |

*Values calculated according to Colby

TABLE A-1-83

|  | Application rate g of ai/ha | Bromus secalinus observed | Bromus secalinus calculated* |
|---|---|---|---|
| I-2 | 8 | 80 |  |
|  | 4 | 70 |  |
| thifensulfuron-methyl | 15 | 0 |  |
|  | 8 | 0 |  |
| I-2 + | 8 + 15 | 98 | 80 |
| thifensulfuron-methyl | 4 + 15 | 98 | 70 |
|  | 8 + 8 | 98 | 80 |
|  | 4 + 8 | 98 | 70 |

TABLE A-1-84

|  | Application rate g of ai/ha | Eriochloa villosa observed | Eriochloa villosa calculated* |
|---|---|---|---|
| I-2 | 8 | 90 |  |
| thifensulfuron-methyl | 15 | 10 |  |
| I-2 + thifensulfuron-methyl | 8 + 15 | 98 | 91 |

*Values calculated according to Colby

TABLE A-1-85

|  | Application rate g of ai/ha | Bromus secalinus observed | Bromus secalinus calculated* |
|---|---|---|---|
| I-2 | 8 | 80 |  |
|  | 4 | 70 |  |
|  | 2 | 70 |  |
| tribenuron-methyl | 8 | 0 |  |
|  | 4 | 0 |  |
| I-2 + | 8 + 8 | 95 | 80 |
| tribenuron-methyl | 4 + 8 | 95 | 70 |
|  | 2 + 8 | 90 | 70 |
|  | 8 + 4 | 95 | 80 |
|  | 4 + 4 | 90 | 70 |
|  | 2 + 4 | 90 | 70 |

TABLE A-1-86

|  | Application rate g of ai/ha | Cyperus esculentus observed | Cyperus esculentus calculated* |
|---|---|---|---|
| I-2 | 8 | 70 |  |
|  | 4 | 60 |  |
|  | 2 | 40 |  |
| tribenuron-methyl | 8 | 0 |  |
|  | 4 | 0 |  |
| I-2 + | 8 + 8 | 90 | 70 |
| tribenuron-methyl | 4 + 8 | 70 | 60 |
|  | 2 + 8 | 70 | 40 |
|  | 8 + 4 | 80 | 70 |
|  | 4 + 4 | 70 | 60 |
|  | 2 + 4 | 70 | 40 |

*Values calculated according to Colby

TABLE A-1-87

|  | Application rate g of ai/ha | Veronica persicaria observed | Veronica persicaria calculated* |
|---|---|---|---|
| I-2 | 8 | 30 |  |
|  | 4 | 30 |  |
| tribenuron-methyl | 4 | 90 |  |

TABLE A-1-87-continued

| | Application rate g of ai/ha | Veronica persicaria observed | Veronica persicaria calculated* |
|---|---|---|---|
| I-2 + | 8 + 4 | 98 | 93 |
| tribenuron-methyl | 4 + 4 | 98 | 93 |

TABLE A-1-88

| | Application rate g of ai/ha | Bromus secalinus observed | Bromus secalinus calculated* |
|---|---|---|---|
| I-2 | 8 | 80 | |
| | 4 | 70 | |
| | 2 | 70 | |
| HWH 4991 | 60 | 30 | |
| | 30 | 20 | |
| I-2 + | 8 + 60 | 100 | 86 |
| HWH 4991 | 4 + 60 | 100 | 79 |
| | 2 + 60 | 95 | 79 |
| | 8 + 30 | 99 | 84 |
| | 4 + 30 | 99 | 76 |
| | 2 + 30 | 95 | 76 |

*Values calculated according to Colby

TABLE A-1-89

| | Application rate g of ai/ha | Veronica persicaria observed | Veronica persicaria calculated* |
|---|---|---|---|
| I-2 | 8 | 30 | |
| | 4 | 30 | |
| | 2 | 0 | |
| HWH 4991 | 30 | 90 | |
| I-2 + | 8 + 30 | 100 | 93 |
| HWH 4991 | 4 + 30 | 100 | 93 |
| | 2 + 30 | 100 | 90 |

TABLE A-1-90

| | Application rate g of ai/ha | Lolium perenne observed | Lolium perenne calculated* |
|---|---|---|---|
| I-2 | 2 | 80 | |
| HWH 4991 | 60 | 60 | |
| | 30 | 20 | |
| I-2 + | 2 + 60 | 98 | 92 |
| HWH 4991 | 2 + 30 | 95 | 84 |

*Values calculated according to Colby

TABLE A-1-91

| | Application rate g of ai/ha | Alopecurus myosuroides observed | Alopecurus myosuroides calculated* |
|---|---|---|---|
| I-2 | 4 | 80 | |
| | 2 | 80 | |
| sulfosate | 250 | 30 | |
| I-2 + | 4 + 250 | 95 | 86 |
| sulfosate | 2 + 250 | 95 | 86 |

TABLE A-1-92

| | Application rate g of ai/ha | Lolium perenne observed | Lolium perenne calculated* |
|---|---|---|---|
| I-2 | 4 | 70 | |
| | 2 | 70 | |
| sulfosate | 250 | 70 | |
| I-2 + | 4 + 250 | 98 | 91 |
| sulfosate | 2 + 250 | 98 | 91 |

*Values calculated according to Colby

TABLE A-1-93

| | Application rate g of ai/ha | Lolium perenne observed | Lolium perenne calculated* |
|---|---|---|---|
| I-2 | 8 | 90 | |
| | 4 | 70 | |
| | 2 | 70 | |
| tritosulfuron | 30 | 0 | |
| | 15 | 0 | |
| I-2 + | 8 + 30 | 98 | 90 |
| tritosulfuron | 4 + 30 | 98 | 70 |
| | 2 + 30 | 90 | 70 |
| | 8 + 15 | 98 | 90 |
| | 4 + 15 | 95 | 70 |
| | 2 + 15 | 95 | 70 |

TABLE A-1-94

| | Application rate g of ai/ha | Setaria viridis observed | Setaria viridis calculated* |
|---|---|---|---|
| I-2 | 8 | 95 | |
| | 4 | 90 | |
| | 2 | 90 | |
| tritosulfuron | 30 | 0 | |
| I-2 + | 8 + 30 | 99 | 95 |
| tritosulfuron | 4 + 30 | 95 | 90 |
| | 2 + 30 | 95 | 90 |

*Values calculated according to Colby

TABLE A-1-95

| | Application rate g of ai/ha | Digitaria sanguinalis observed | Digitaria sanguinalis calculated* |
|---|---|---|---|
| I-2 | 8 | 90 | |
| tritosulfuron | 30 | 40 | |
| | 15 | 30 | |
| I-2 + | 8 + 30 | 98 | 94 |
| tritosulfuron | 8 + 15 | 98 | 93 |

TABLE A-1-96

| | Application rate g of ai/ha | Lolium perenne observed | Lolium perenne calculated* |
|---|---|---|---|
| I-2 | 8 | 90 | |
| | 4 | 70 | |
| | 2 | 70 | |
| SLA 5599 | 60 | 30 | |
| | 30 | 0 | |
| I-2 + | 8 + 60 | 99 | 93 |
| SLA 5599 | 4 + 60 | 98 | 79 |
| | 2 + 60 | 95 | 79 |
| | 8 + 30 | 99 | 90 |

TABLE A-1-96-continued

| | Application rate g of ai/ha | Lolium perenne observed | Lolium perenne calculated* |
|---|---|---|---|
| | 4 + 30 | 98 | 70 |
| | 2 + 30 | 90 | 70 |

*Values calculated according to Colby

TABLE A-1-97

| | Application rate g of ai/ha | Avena fatua observed | Avena fatua calculated* |
|---|---|---|---|
| I-2 | 4 | 90 | |
| | 2 | 80 | |
| SLA 5599 | 60 | 0 | |
| | 30 | 0 | |
| I-2 + | 4 + 60 | 95 | 90 |
| SLA 5599 | 2 + 60 | 90 | 80 |
| | 4 + 30 | 95 | 90 |
| | 2 + 30 | 90 | 80 |

TABLE A-1-98

| | Application rate g of ai/ha | Veronica persicaria observed | Veronica persicaria calculated* |
|---|---|---|---|
| I-2 | 8 | 40 | |
| | 4 | 0 | |
| SLA 5599 | 30 | 80 | |
| I-2 + | 8 + 30 | 100 | 88 |
| SLA 5599 | 4 + 30 | 98 | 80 |

*Values calculated according to Colby

TABLE A-1-99

| | Application rate g of ai/ha | Bromus secalinus observed | Bromus secalinus calculated* |
|---|---|---|---|
| I-2 | 4 | 90 | |
| | 2 | 80 | |
| pyraflufen-ethyl | 4 | 30 | |
| | 2 | 30 | |
| I-2 + | 4 + 4 | 98 | 93 |
| pyraflufen-ethyl | 2 + 4 | 98 | 86 |
| | 4 + 2 | 98 | 93 |
| | 2 + 2 | 95 | 86 |

TABLE A-1-100

| | Application rate g of ai/ha | Lolium perenne observed | Lolium perenne calculated* |
|---|---|---|---|
| I-2 | 8 | 90 | |
| | 4 | 70 | |
| | 2 | 70 | |
| pyraflufen-ethyl | 4 | 30 | |
| | 2 | 0 | |
| I-2 + | 8 + 4 | 99 | 93 |
| pyraflufen-ethyl | 4 + 4 | 95 | 79 |
| | 2 + 4 | 95 | 79 |
| | 8 + 2 | 99 | 90 |
| | 4 + 2 | 95 | 70 |
| | 2 + 2 | 90 | 70 |

*Values calculated according to Colby

TABLE A-1-101

| | Application rate g of ai/ha | Setria viridis observed | Setria viridis calculated* |
|---|---|---|---|
| I-2 | 4 | 90 | |
| | 2 | 90 | |
| pyraflufen ethyl | 4 | 40 | |
| | 2 | 40 | |
| I-2 + | 4 + 4 | 98 | 94 |
| pyraflufen ethyl | 2 + 4 | 98 | 94 |
| | 4 + 2 | 98 | 94 |
| | 2 + 2 | 98 | 94 |

TABLE A-1-102

| | Application rate g of ai/ha | Bromus secalinus observed | Bromus secalinus calculated* |
|---|---|---|---|
| I-2 | 8 | 80 | |
| flufenacet | 125 | 40 | |
| | 60 | 20 | |
| | 30 | 0 | |
| I-2 + | 8 + 125 | 100 | 88 |
| flufenacet | 8 + 60 | 99 | 84 |
| | 8 + 30 | 99 | 80 |

*Values calculated according to Colby

TABLE A-1-103

| | Application rate g of ai/ha | Polygonum convolvolus observed | Polygonum convolvolus calculated* |
|---|---|---|---|
| I-2 | 8 | 90 | |
| | 4 | 80 | |
| | 2 | 70 | |
| flufenacet | 125 | 0 | |
| | 60 | 0 | |
| | 30 | 0 | |
| I-2 + | 8 + 125 | 98 | 90 |
| flufenacet | 4 + 125 | 90 | 80 |
| | 2 + 125 | 80 | 70 |
| | 8 + 60 | 98 | 90 |
| | 4 + 60 | 90 | 80 |
| | 2 + 60 | 80 | 70 |
| | 8 + 30 | 98 | 90 |
| | 4 + 30 | 90 | 80 |
| | 2 + 30 | 80 | 70 |

*Values calculated according to Colby

TABLE A-1-104

| | Application rate g of ai/ha | Chenopodium album observed | Chenopodium album calculated* |
|---|---|---|---|
| I-2 | 2 | 70 | |
| flufenacet | 125 | 0 | |
| | 60 | 0 | |
| | 30 | 0 | |
| I-2 + | 2 + 125 | 95 | 70 |
| flufenacet | 2 + 60 | 95 | 70 |
| | 2 + 30 | 90 | 70 |

*Values calculated according to Colby

We claim:

1. A herbicidal composition comprising an active compound combination comprising:
   (a) a substituted thien-3-yl-sulphonylaminocarbonyltriazolinone of formula (I-2)

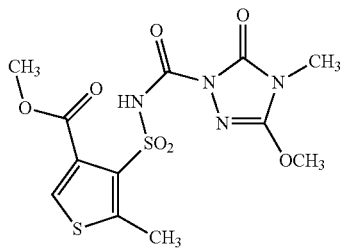 (I-2)

or salts thereof;
(b) foramsulfuron; and
(c) halosulfuron-methyl.

2. The composition according to claim 1, wherein the substituted thien-3-yl-sulphonylamino(thio)carbonyltriazolin(ethi)one of formula (I-2) is in the form of a sodium, potassium, magnesium, calcium, ammonium, $C_1$-$C_4$-alkylammonium, di-($C_1$-$C_4$-alkyl)ammonium, tri-($C_1$-$C_4$-alkyl)ammonium, tetra-($C_1$-$C_4$-alkyl)ammonium, tri-($C_1$-$C_4$-alkyl)sulphonium, $C_5$- or $C_6$-cycloalkylammonium, or di-($C_1$-$C_2$-alkyl)benzylammonium salt.

3. The composition according to claim 1, wherein the substituted thien-3-yl-sulphonylamino(thio)carbonyltriazolin(ethi)one of formula (I-2) is in the form of a sodium salt.

4. A method for controlling unwanted plants, the method comprising applying an effective amount of a composition according to claim 1 to the unwanted plants and/or their habitat.

* * * * *